(12) United States Patent
Hatch et al.

(10) Patent No.: US 12,274,799 B2
(45) Date of Patent: Apr. 15, 2025

(54) MICROBIAL DECONTAMINATION OF COMMON TOUCH ARTICLES

(71) Applicant: Ecolab USA Inc., St. Paul, MN (US)

(72) Inventors: Steven Randall Hatch, Prior Lake, MN (US); Paul Dominic Christian, Apple Valley, MN (US); Paul R. Kraus, Apple Valley, MN (US)

(73) Assignee: Ecolab USA Inc., St. Paul, MN (US)

( * ) Notice: Subject to any disclaimer, the term of this patent is extended or adjusted under 35 U.S.C. 154(b) by 646 days.

(21) Appl. No.: 17/325,440

(22) Filed: May 20, 2021

(65) Prior Publication Data

US 2021/0369891 A1    Dec. 2, 2021

Related U.S. Application Data

(60) Provisional application No. 63/031,931, filed on May 29, 2020.

(51) Int. Cl.
| | |
|---|---|
| *A61L 2/10* | (2006.01) |
| *A61L 2/08* | (2006.01) |
| *A61L 2/24* | (2006.01) |
| *A61L 2/26* | (2006.01) |
| *G05B 15/02* | (2006.01) |

(52) U.S. Cl.
CPC ............ *A61L 2/10* (2013.01); *A61L 2/24* (2013.01); *A61L 2/26* (2013.01); *G05B 15/02* (2013.01); *A61L 2202/11* (2013.01); *A61L 2202/121* (2013.01); *A61L 2202/122* (2013.01); *A61L 2202/14* (2013.01)

(58) Field of Classification Search
CPC .................................. A61L 2/084; A61L 2/10
See application file for complete search history.

(56) References Cited

U.S. PATENT DOCUMENTS

| | | |
|---|---|---|
| 5,755,103 A | 5/1998 | Na et al. |
| 6,524,529 B1 | 2/2003 | Horton, III |
| 6,573,663 B1 | 6/2003 | MacGregor et al. |

(Continued)

FOREIGN PATENT DOCUMENTS

| | | |
|---|---|---|
| CN | 1653305 A | 8/2005 |
| CN | 101452358 A | 6/2009 |

(Continued)

OTHER PUBLICATIONS

Notice of Allowance from U.S. Appl. No. 16/818,138 dated Oct. 20, 2022, 10 pp.

(Continued)

*Primary Examiner* — Kevin Joyner
(74) *Attorney, Agent, or Firm* — Shumaker & Sieffert, P.A.

(57) ABSTRACT

An antimicrobial lighting system includes an antimicrobial lighting array that emits antimicrobial light within one or more antimicrobial wavelength ranges to inactivate one or more microorganisms on common touch surfaces. The common touch surfaces may include, for example, restaurant menus, airline safety instructions, pamphlets, instruction cards, or other common touch objects having a generally flat form factor, or that can be reduced to a flat form factor. Application of the antimicrobial light to the common touch surfaces may improve hygiene of such common touch surfaces and may help maintain microbial growth below acceptable levels.

21 Claims, 6 Drawing Sheets

(56) References Cited

U.S. PATENT DOCUMENTS

| | | |
|---|---|---|
| 7,270,195 B2 | 9/2007 | MacGregor et al. |
| 8,182,744 B2 | 5/2012 | Mlodzinski et al. |
| 8,398,264 B2 | 3/2013 | Anderson et al. |
| 8,458,954 B2 | 6/2013 | Yamada et al. |
| 8,581,882 B2 | 11/2013 | Sohn et al. |
| 9,039,966 B2 | 5/2015 | Anderson et al. |
| 9,700,641 B2 | 7/2017 | Hawkins et al. |
| 9,839,706 B2 | 12/2017 | Anderson et al. |
| 9,963,597 B2 | 5/2018 | Aizenberg et al. |
| 10,232,066 B2 | 3/2019 | Bailey |
| 10,773,690 B2 | 9/2020 | Dellock et al. |
| 11,819,581 B2 | 11/2023 | Kraus et al. |
| 2002/0189270 A1 | 12/2002 | Stensrud et al. |
| 2004/0175290 A1 | 9/2004 | Scheir et al. |
| 2006/0021375 A1 | 2/2006 | Wetzel et al. |
| 2010/0303671 A1 | 12/2010 | Bertrand |
| 2011/0216042 A1 | 9/2011 | Wassvik et al. |
| 2012/0228645 A1 | 9/2012 | Tu et al. |
| 2013/0224086 A1 | 8/2013 | Stibich et al. |
| 2013/0291735 A1 | 11/2013 | Livchak et al. |
| 2014/0060096 A1 | 3/2014 | Shur et al. |
| 2014/0060104 A1 | 3/2014 | Shur et al. |
| 2014/0061509 A1 | 3/2014 | Shur et al. |
| 2014/0079587 A1 | 3/2014 | Dayton |
| 2014/0119985 A1 | 5/2014 | Berg et al. |
| 2014/0264076 A1 | 9/2014 | Bettles et al. |
| 2014/0300581 A1 | 10/2014 | Aurongzeb et al. |
| 2015/0069265 A1 | 3/2015 | Smetona et al. |
| 2015/0182647 A1 | 7/2015 | Ranta et al. |
| 2016/0271803 A1 | 9/2016 | Stewart |
| 2016/0375161 A1 | 12/2016 | Hawkins et al. |
| 2017/0095585 A1 | 4/2017 | Smetona et al. |
| 2017/0100989 A1 | 4/2017 | Chapaton et al. |
| 2017/0246331 A1 | 8/2017 | Lloyd |
| 2017/0333582 A1 | 11/2017 | Davis |
| 2017/0340761 A1 | 11/2017 | Shur et al. |
| 2017/0368213 A1 | 12/2017 | Mintie et al. |
| 2018/0023821 A1 | 1/2018 | Kim et al. |
| 2018/0046166 A1 | 2/2018 | Kumar et al. |
| 2018/0113066 A1 | 4/2018 | Freitag et al. |
| 2018/0117189 A1 | 5/2018 | Yadav et al. |
| 2018/0117190 A1 | 5/2018 | Bailey |
| 2018/0117193 A1 | 5/2018 | Yadav et al. |
| 2018/0124883 A1 | 5/2018 | Bailey |
| 2018/0126021 A1 | 5/2018 | Valentine et al. |
| 2018/0140727 A1 | 5/2018 | Romo et al. |
| 2018/0154027 A1 | 6/2018 | Anderson et al. |
| 2018/0193501 A1 | 7/2018 | Ufkes |
| 2018/0243452 A1 | 8/2018 | Hawkins et al. |
| 2018/0243453 A1 | 8/2018 | Hawkins et al. |
| 2018/0345485 A1 | 12/2018 | Sinnet et al. |
| 2019/0001930 A1 | 1/2019 | Dellock et al. |
| 2019/0176338 A1 | 6/2019 | Zito et al. |
| 2019/0298871 A1 | 10/2019 | Dobrinsky |
| 2020/0205926 A1 | 7/2020 | Keibel |
| 2020/0254122 A1* | 8/2020 | Starkweather ............ A61L 2/10 |
| 2020/0289683 A1 | 9/2020 | Christian et al. |
| 2021/0000991 A1 | 1/2021 | Kraus et al. |
| 2021/0308317 A1* | 10/2021 | Chen .......................... A61L 9/20 |

FOREIGN PATENT DOCUMENTS

| | | |
|---|---|---|
| CN | 101622016 A | 1/2010 |
| CN | 102014608 A | 4/2011 |
| CN | 1103402552 A | 11/2013 |
| CN | 204121454 U | 1/2015 |
| CN | 104704067 A | 6/2015 |
| CN | 105142682 B | 12/2015 |
| CN | 105163605 B | 12/2015 |
| CN | 204864170 U | 12/2015 |
| CN | 105856259 A | 8/2016 |
| CN | 105879148 A | 8/2016 |
| CN | 105963730 A | 9/2016 |
| CN | 205747250 U | 11/2016 |
| CN | 106272467 A | 1/2017 |
| CN | 206085069 U | 4/2017 |
| CN | 206795846 U | 12/2017 |
| CN | 108068125 A | 5/2018 |
| CN | 207710799 U | 8/2018 |
| CN | 108606754 A | 10/2018 |
| CN | 108714884 A | 10/2018 |
| CN | 109065186 A | 12/2018 |
| CN | 106444564 B | 1/2019 |
| CN | 109131234 A | 1/2019 |
| CN | 109202939 A | 1/2019 |
| CN | 109276728 A | 1/2019 |
| CN | 109316612 A | 2/2019 |
| CN | 109431810 A | 3/2019 |
| CN | 109481707 A | 3/2019 |
| CN | 109481708 A | 3/2019 |
| DE | 102017209966 A1 | 12/2018 |
| EP | 3355940 A2 | 8/2018 |
| JP | 2015502804 A | 1/2015 |
| JP | 2015167470 A | 9/2015 |
| JP | 2018117586 A | 8/2018 |
| KR | 1499359 B1 | 3/2015 |
| KR | 1724447 B1 | 4/2017 |
| KR | 20180010824 A | 1/2018 |
| KR | 20190054955 A | 5/2019 |
| WO | 2003096387 A2 | 11/2003 |
| WO | 2006124211 A1 | 11/2006 |
| WO | 2014036080 A1 | 3/2014 |
| WO | 2015051024 A1 | 4/2015 |
| WO | 2014036080 A9 | 5/2015 |
| WO | 2017062260 A2 | 4/2017 |
| WO | 2018087171 A1 | 5/2018 |
| WO | 2018122009 A1 | 7/2018 |

OTHER PUBLICATIONS

Response to Office Action dated Aug. 22, 2022 from U.S. Appl. No. 16/918,644, filed Nov. 22, 2022, 12 pp.

Advisory Action from U.S. Appl. No. 16/918,644, dated Apr. 17, 2023, 2 pp.

Response to Final Office Action dated Feb. 6, 2023 from U.S. Appl. No. 16/918,644, filed Apr. 4, 2023, 12 pp.

Response to Communication Pursuant to Rules 161(1) and 162 EPC dated Jan. 11, 2023, from counterpart European Application No. 21732722.0, filed Jun. 26, 2023, 19 pp.

Notice of Allowance from U.S. Appl. No. 16/918,644 dated Jul. 14, 2023, 12 pp.

"Hubbell Lighting Secures Licensing Agreement with the University of Strathclyde High Intensity Narrow Spectrum Technology," Hubbell Lighting, May 4, 2018, 3 pp.

"Hubbell Lighting to Integrate Bacteria Suppressing Technology into Smart Luminaires," http://www.lightingdesignandspecification.ca/changing-scene/2322-hubbe, Jun. 1, 2018, 1 pp.

"Ice UV," retrieved from https://www.freshaireuv.com/ice-machines/ on Feb. 22, 2019, 5 pp.

"LG Electronics LP153HD3B Installation Guide," retrieved from manualzz.com/doc/4030343/lg-electronics-lp153hd3b-installation-guide on May 11, 2020, 2 pp.

"Light Fixture Kills Bacteria Safely, Continuously," Science Daily, Jun. 26, 2015, 2 pp.

"Single Color Outdoor Weatherproof LED Flexible Lightstrip Part Number WFLS-x," https://d114hh0cykhyb0.cloudfront.net/pdfs/WFLS-x.pdf, Apr. 21, 2014, 2 pp.

"Wireless LED 4 Channel EZ Dimmer Controller with Channel Pairing," https://www.superbrightleds.comjmoreinfojrgb-led-controllers/wireless-4-channelrgb-led-dimmer-receiver/3372/7141/#tab/Reviews, Jul. 17, 2018, 7 pp.

Endarko et al., "High-Intensity 405 nm Light Inactivation of Listeria Monocytogenes," Photochemistry and Photobiology, vol. 88, No. 5, Sep.-Oct. 2012, pp. 1280-1286.

Gunther et al., "The Effects of 405-nm Visible Light on the Survival of Campylobacter on Chicken Skin and Stainless Steel," Foodborne Pathogens and Disease, vol. 13, No. 5, May 2016, 6 pp.

Kim et al., "Antibacterial Effect and Mechanism of High-Intensity 405 ± 5 nm Light Emitting Diode on Bacillus Cereus, Listeria Monocytogenes, and *Staphylococcus aureus* Under Refrigerated

(56) References Cited

OTHER PUBLICATIONS

Condition," Journal of Photochemistry and Photobiology B: Biology, vol. 153, Dec. 2015, pp. 33-39.
Kingsley et al., "Evaluation of 405-nm Monochromatic Light for Inactivation of Tulane Virus on Blueberry Surfaces," Journal of Applied Microbiology, vol. 124, No. 4, Apr. 2018, pp. 1017-1022.
Lacombe et al., "Reduction of Bacterial Pathogens and Potential Surrogates on the Surface of Almonds Using High-Intensity 405-nanometer light," Journal of Food Protection, vol. 79, No. 11, Nov. 2016, pp. 1840-1845.
Liang et al., "Blue Light Induced Free Radicals from Riboflavin on *E. coli* DNA Damage," Journal of Photochemistry and Photobiology B: Biology, vol. 119, Dec. 29, 2012, pp. 60-64.
MacLean et al., "High-Intensity Narrow-Spectrum Light Inactivation and Wavelength Sensitivity of *Staphylococcus aureus*," Federation of European Microbiological Societies, Jun. 16, 2008, pp. 227-232.
MacLean et al., "Sporicidal Effects of High-Intensity 405 nm Visible Light on Endospore-Forming Bacteria," Photochemistry and Photobiology, vol. 89, No. 1, Jan./Feb. 2013, pp. 120-126.
McDonald et al., "405 nm Light Exposure of Osteoblasts and Inactivation of Bacterial Isolates from Arthroplasty Patients: Potential for New Disinfection Applications?", European Cells and Materials, vol. 25, Mar. 7, 2013, pp. 204-214.
Murdoch et al., "Bactericidal Effects of 405nm Light Exposure Demonstrated by Inactivation of *Escherichia, Salmonella, Shigella, Listeria,* and *Mycobacterium* Species in Liquid Suspensions and on Exposed Surfaces," The Scientific World Journal, vol. 2012, Apr. 1, 2012, 8 pp.
Murdoch et al., "Inactivation of Campylobacter Jejuni by Exposure to High-Intensity 405-nm Visible Light," Foodborne Pathogens and Disease, vol. 7, No. 10, Oct. 2010, pp. 1211-1216.
Ramakrishnan et al., "Differential Sensitivity of Osteoblasts and Bacterial Pathogens to 405-nm Light Highlighting Potential for Decontamination Applications in Orthopedic Surgery," Journal of Biomedical Optics, vol. 9, No. 10, Oct. 2014, 8 pp.
Roh et al., "Blue Light-Emitting Diode Photoinactivation Inhibits Edwardsiellosis in Fancy Carp (*Cyprinus carpio*)," Aquaculture, vol. 483, Jan. 20, 2018, pp. 1-7.
U.S. Appl. No. 17/101,449, filed Nov. 23, 2020, by Finison.
U.S. Appl. No. 17/325,398, filed May 20, 2021, by Voss et al.
International Search Report and Written Opinion of International Application No. PCT/US2021/033326, mailed Sep. 24, 2021, 18 pp.
Office Action from U.S. Appl. No. 16/918,644 dated Aug. 22, 2022, 14 pp.
Response to Office Action dated May 24, 2022 from U.S. Appl. No. 16/818,138, filed Aug. 24, 2022, 14 pp.
Office Action from U.S. Appl. No. 16/818,138, dated May 24, 2022, 13 pp.
Final Office Action from U.S. Appl. No. 16/918,644 dated Feb. 6, 2023, 18 pp.
Response to Office Action dated May 16, 2024 from U.S. Appl. No. 18/494,121, filed Aug. 6, 2024, 9 pp.
Notice of Allowance from U.S. Appl. No. 17/325,398 dated Aug. 19, 2024, 9 pp.
Notice of Allowance from U.S. Appl. No. 17/325,398 dated Aug. 28, 2024, 6 pp.
Notice of Allowance from U.S. Appl. No. 18/494,121 dated Aug. 21, 2024, 11 pp.
Response to Communication pursuant to Article 94(3) EPC dated Apr. 29, 2024, from counterpart European Application No. 21732722.0 filed Aug. 27, 2024, 30 pp.
Communication pursuant to Article 94(3) EPC from counterpart European Application No. 21732722.0 dated Apr. 29, 2024, 6 pp.
English Translation of Document ID No. KR 20180010824 provided by the European Patent Office website Espacenet.com: Kim Tae Young; Air Conditioner; Jan. 31, 2018, 19 pp.
Office Action from U.S. Appl. No. 17/325,398 dated Apr. 22, 2024, 14 pp.
Office Action from U.S. Appl. No. 18/494,121 dated May 16, 2024, 10 pp.
superbrightleds.com, "180° optics improve visibility with wider area illumination LED Lighting For Everything Weatherproof LED Flexible Light Strip Single Color Outdoor", Apr. 21, 2014, p. 2, Retrieved at: https://d114hh0cykhyb0.cloudfront.net/pdfs/WFLS-x.pdf.
superbrightleds.com, "Wireless LED 4 Channel EZ Dimmer Controller w/ Channel Pairing | Super Bright LEDs", Jul. 17, 2018, p. 15, Retrieved at: https://www.superbrightleds.com/moreinfo/rgb-led-controllers/wireless-4-channel-rgb-led-dimmer-receiver/3372/7141/#tab/Reviews.
Response to Office Action mailed Apr. 22, 2024, from U.S. Appl. No. 17/325,398, filed Jul. 12, 2024, 10 pp.
Notifice of Reasons for Refusal, and translation thereof, from counterpart Japanse Application No. 2022-573271 dated Jan. 7, 2025, 13 pp.
First Office Action and Search Report, and translation thereof, from counterpart Chinese Application No. 202180037132.X dated Jan. 11, 2025, 19 pp.
Communication pursuant to Article 94(3) EPC from counterpart European Application No. 21732722.0 dated Feb. 24, 2025, 7 pp.

\* cited by examiner

MICROBIAL DECONTAMINATION OF COMMON TOUCH ARTICLES

This application claims the benefit of U.S. Provisional Application No. 63/031,931, titled, "MICROBIAL DECONTAMINATION OF COMMON TOUCH ARTICLES", filed May 29, 2020, the entire content of which is incorporated herein by reference.

BACKGROUND

Commonly touched environmental surfaces have been linked to the transmission of pathogens from one person to another through cross-contamination. Common touch surfaces may serve as a reservoir for infectious pathogens and these and other microorganisms may be transmitted directly or indirectly by the hands of the users. For example, reusable common touch objects such as restaurant menus, airline safety instructions and the like are susceptible to repeated deposition and transfer of harmful microorganisms. However, although businesses such as restaurants and airlines may have cleaning protocols in place designed to address this risk, in practice, such articles may be infrequently or inadequately cleaned and/or sanitized.

SUMMARY

In general, the disclosure is directed to systems and/or methods in which antimicrobial light is used to reduce or mitigate microbial growth on common touch surfaces. In some examples, the disclosure is directed to systems and/or methods in which antimicrobial light within one or more antimicrobial wavelength ranges is applied to inactivate one or more microorganisms on one or more common touch surface(s). The common touch surfaces may include, for example, restaurant menus, airline safety instructions, pamphlets, instructions for use (IFUs), credit cards, or surfaces of other common touch objects having a generally flat and/or folded form factor, or that can be reduced to a flat form factor. In other examples, the common touch objects/surfaces may be three-dimensional. Application of the antimicrobial light to inactivate one or more microorganisms on common touch surfaces may help reduce the probability of transmission of microorganisms through cross-contamination of the common touch surfaces.

In another example, the disclosure is directed to systems and/or methods in which a non-thermal (NT) plasma generator is used to reduce or mitigate growth on common touch surfaces. For example, a decontamination device may include an NT plasma generator for inactivation of one or more microorganisms on common touch surfaces.

In one example, the disclosure is directed to a system comprising a lighting array including one or more antimicrobial lighting segments, each antimicrobial lighting segment including one or more light source elements that emit light within one or more antimicrobial wavelength ranges; and a lighting controller comprising: one or more processors; and a data storage device comprising instructions that when executed by the one or more processors cause the one or more processors to: receive object type information associated with a common touch object; and control each antimicrobial lighting segment such that the antimicrobial light array delivers antimicrobial light sufficient to inactivate one or more microorganisms on one or more common touch surface(s) on the common touch object based on the received object type information.

The object type information may be input by a user. The object type information may be indicative that the common touch object is one of a restaurant menu, airline safety instructions, or instructions for use (IFUs). The common touch object may have a flat and/or folded form factor. The one or more processors may activate one or more of the antimicrobial lighting segments and deactivate one or more of the antimicrobial lighting segments based on the object type information.

The system may further comprise a housing including a cover, a base, and one or more sidewalls, the housing defining an enclosed decontamination chamber; the housing further including a slot in one of the sidewalls sized to receive a common touch object, wherein the antimicrobial light segments are arranged to direct antimicrobial light toward a decontamination area within the decontamination chamber, and wherein the common touch object is placed within the decontamination area during an antimicrobial light treatment. The one or more antimicrobial lighting segments may be disposed within the decontamination chamber to direct light at the wavelength and irradiance sufficient to inactivate one or more microorganisms on one or more common touch surfaces on the common touch object.

Each antimicrobial lighting segment may include a substrate and a plurality of light-emitting diode (LED) elements. Each antimicrobial lighting segment may include a substrate and a plurality of light-emitting diode (LED) elements, and wherein each LED element emits antimicrobial light within a first wavelength range of about 380-420 nanometers and having a peak wavelength of about 405 nanometers. The plurality of LED elements may be arranged in a linear pattern on the substrate. The plurality of LED elements may be arranged in a grid pattern on the substrate. The substrate may be one of a flexible substrate or a rigid substrate.

Each antimicrobial lighting segment may include a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-380 nanometers.

Each antimicrobial lighting segment may include a substrate and a plurality of light-emitting diode (LED) elements, wherein one or more of the LED elements emit light within a first antimicrobial wavelength range of about 380-420 nanometers, one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

The data storage device may further comprise instructions that when executed by the one or more processors cause the one or more processors to: receive dimensional information associated with the common touch object; and control each antimicrobial lighting segment such that the antimicrobial light array delivers antimicrobial light sufficient to inactivate one or more microorganisms on one or more common touch surface(s) on the common touch object based on the received dimensional information.

The common touch object may include a first common touch surface and an oppositely facing second common touch surface and wherein the system further comprises a housing forming an enclosed chamber sized to receive the common touch object; and an array of one or more antimicrobial light segments arranged within the chamber to form a first grid pattern of antimicrobial light source elements sized to irradiate the first common touch surface and arranged to form a second grid pattern of antimicrobial light source elements sized to irradiate the second common touch surface. The antimicrobial light segments may be controllable to irradiate the first and second common touch surfaces simultaneously. The antimicrobial light segments may be controllable to irradiate the first and second common touch surfaces in sequence.

In another example, the disclosure is directed to a method comprising disposing a lighting array including one or more antimicrobial lighting segments, each antimicrobial lighting segment including one or more light source elements, wherein each light source element emits antimicrobial light within one or more antimicrobial wavelength ranges; receiving object type information associated with a common touch object; and controlling each antimicrobial lighting segment such that the antimicrobial light array delivers antimicrobial light sufficient to inactivate one or more microorganisms on one or more common touch surface(s) on the common touch object based on the received object type information.

Each antimicrobial lighting segment may include a substrate and a plurality of light-emitting diode (LED) elements, wherein one or more of the LED elements emit light within a first antimicrobial wavelength range of about 380-420 nanometers and having a peak wavelength of about 405 nanometers. One or more of the LED elements may emit light within a second antimicrobial wavelength range of about 200-280 nanometers.

The details of one or more examples are set forth in the accompanying drawings and the description below. Other features and advantages will be apparent from the description and drawings, and from the claims.

DETAILED DESCRIPTION

Figure 1:
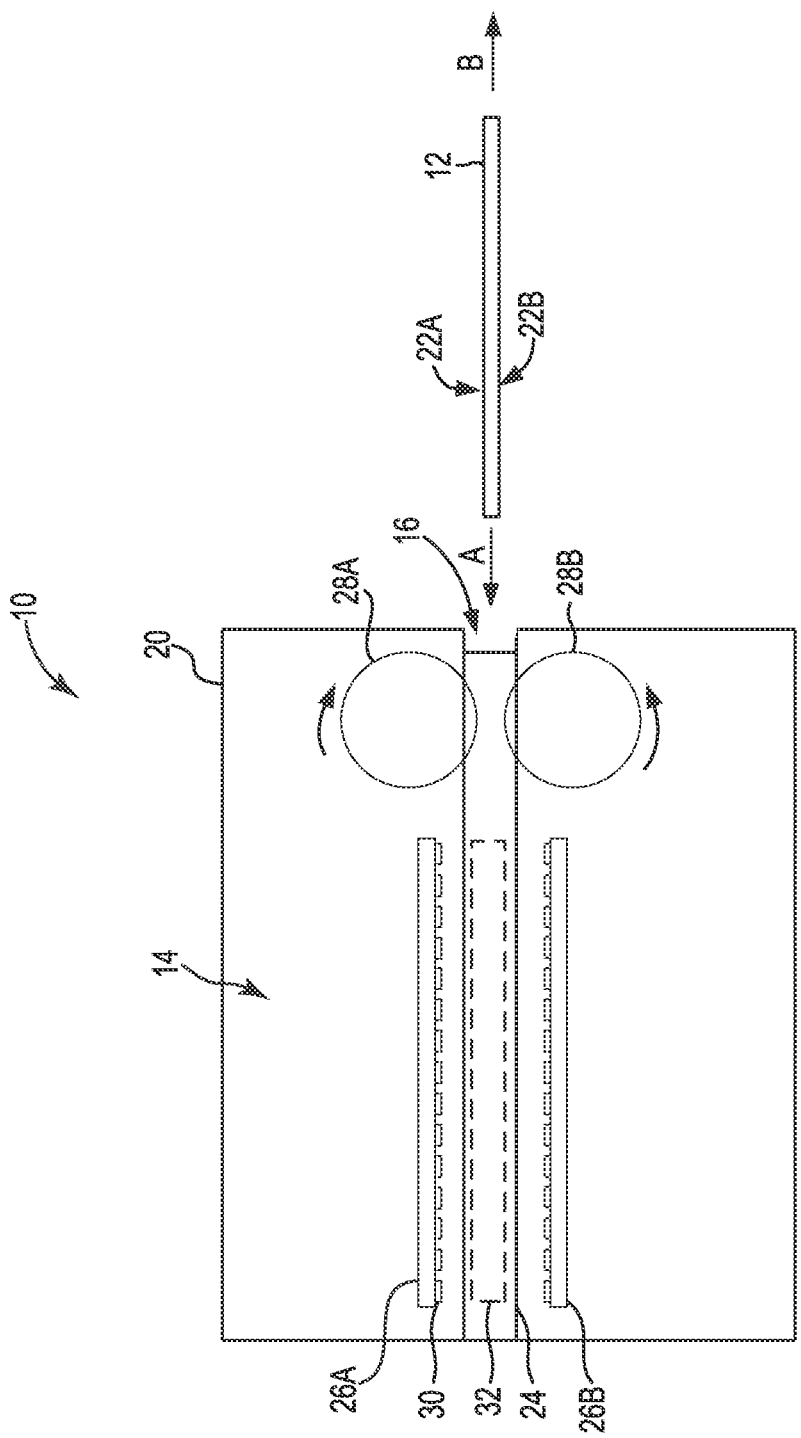
FIG. 1 shows a cross-sectional side view of an example decontamination device including multiple antimicrobial light segments for inactivation of one or more microorganisms on common touch surfaces in accordance with the present disclosure.

In general, in some examples, the disclosure is directed to systems and/or methods in which antimicrobial light is used to reduce or mitigate microbial growth on common touch surfaces. For example, the disclosure is directed to systems and/or methods in which antimicrobial light within one or more antimicrobial wavelength ranges is applied to inactivate one or more microorganisms on common touch surfaces. The common touch surfaces may include, for example, restaurant menus, airline safety instructions, pamphlets, instruction cards, or other common touch objects having a generally flat form factor, or that can be reduced to a flat form factor. Application of the antimicrobial light to inactivate one or more microorganisms on common touch surfaces may help reduce the probability of transmission of microorganisms through cross-contamination of the common touch surfaces.

In another example, the disclosure is directed to systems and/or methods in which a non-thermal (NT) plasma generator is used to reduce or mitigate growth on common touch surfaces. For example, a decontamination device may include an NT plasma generator for inactivation of one or more microorganisms on common touch surfaces.

The antimicrobial light may include light within a first antimicrobial wavelength range of 380-420 nanometers (nm), and/or light within a second antimicrobial wavelength range, such as ultraviolet light within a wavelength range of 10-400 nanometers (nm). In some examples, the antimicrobial light within the first wavelength range has a peak wavelength of about 405 nm. In some examples, the antimicrobial light within the second wavelength range may include ultraviolet A (UVA) light within a wavelength range of 315-400 nm, ultraviolet B (UVB) light within a wavelength range of 280-315 nm and/or ultraviolet C (UVC) light within a wavelength range of 200-280 nm. Application of the antimicrobial light may improve hygiene and reduce growth of microorganisms on one or more surfaces of the common touch objects. In some examples, the systems and/or methods may complement manual cleaning procedures, such as spraying and/or wiping down, and help reduce the probability that microorganisms will be transmitted through cross-contamination of the common touch surfaces.

Although the disclosure will generally discuss antimicrobial lighting for reduction of microbial growth on common touch surfaces such as restaurant menus, airline instruction cards, and other common touch objects having a generally flat and/or folded form factor, it shall be understood that the antimicrobial lighting arrays of the present disclosure may also be used to reduce microbial growth in other types of common touch objects having similar form factors, and that the disclosure is not limited in this respect. For example, the antimicrobial lighting arrays may also be used to reduce microbial growth on credit cards, envelopes, letters, handheld bar code scanners used in self-check-out aisles, separation bars used at grocery store check-outs to demark one customer's items from another, restaurant table number placards or electronic "pucks" given to customers waiting to be seated, reusable cloth napkins or other reusable textiles, and any other common touch object that is susceptible to microbial growth or that could benefit from mitigation or reduction of microbial growth.

Light having wavelengths in a range of about 380-420 nm has been demonstrated to decontaminate the air and exposed surfaces by inactivating microorganisms and pathogens. For purposes of the present disclosure, in some examples, the term "antimicrobial light" includes light within a first wavelength range of about 380-420 nm. In some examples, the antimicrobial light within the first wavelength range has a peak wavelength of about 405 nm. The antimicrobial light has sufficient irradiance (power received by a target surface per unit area) of these wavelengths to result in inactivation of one or more microorganisms at the target surface within a desired period of time. In some examples, antimicrobial light source(s) may include one or more light source elements, such as light-emitting diodes (LEDs), that emit light within the first wavelength range of about 380-420 nm. In some examples, the antimicrobial light within the first wavelength range emitted by the LEDs has a peak wavelength of about 405 nm. It shall be understood that the particular range of wavelengths emitted by the light source element(s) may vary somewhat from these stated ranges, depending, for example, on the response curve for each particular light source element, and the disclosure is not limited in this respect. Also, each light source element does not necessarily emit light across the entire wavelength range. In general, the antimicrobial light contains at least some of these wavelengths at a sufficient intensity to inactivate one or more microorganisms on a target surface within a desired period of time.

In some other examples, the "antimicrobial light" may include light within a second wavelength range, wherein the second wavelength range includes ultraviolet light within a wavelength range of 10-400 nanometers (nm). The ultraviolet light may include ultraviolet A (UVA) light within a wavelength range of 315-400 nm, ultraviolet B (UVB) light within a wavelength range of 280-315 nm and/or ultraviolet C (UVC) light within a wavelength range of 200-280 nm. The intensity of the ultraviolet light has sufficient irradiance (power received by a target surface per unit area) of these wavelengths to result in inactivation of one or more microorganisms at the target surface within a desired period of time. In some examples, the light source elements that emit light within the second antimicrobial wavelength range include light-emitting diodes (LEDs). The light of the first wavelength range and the light of the second wavelength range may be emitted by the same light source elements or by different light source elements.

The spectral energy of the combined antimicrobial light (that is, the light of the first wavelength range combined with the light of the second wavelength range) may be designed such that the proportion of spectral energy of light in the first wavelength range and the proportion of spectral energy within the second wavelength range is optimized with respect to the type of microorganisms targeted, the amount of time required to sufficiently inactivate the targeted microorganisms, to minimize damage such as fading or other degradation of the target surfaces, to minimize human exposure to certain wavelengths of antimicrobial light, the occupancy of the room, and/or other factors which may influence the relative amount of the antimicrobial wavelengths to be applied. For example, in some applications, the combined light may be designed such that at least 30% of the spectral energy of the combined light is within the first wavelength range and at least 30% of the spectral energy of the combined light is within the second wavelength range.

Light elements within the second antimicrobial wavelength range can include one or more of UVA, UVB and/or UVC wavelengths, and these may be used in conjunction with or independently of light elements that emit light within the first antimicrobial wavelength range of 380-420 nm. The light elements of the second antimicrobial wavelength range may be interspersed throughout the array can be activated in such manner that they are cycled sequentially, pulsed independent of the light elements of the first antimicrobial wavelength range, operated at different power settings, etc.

For combined light (that is, the light of the first wavelength range combined with the light of the second wavelength range), the proportion of spectral energy of light in the first wavelength range may be such that at least 30% of the spectral energy of the combined light is within the first wavelength range, at least 30% of the spectral energy of the combined light is within the second wavelength range.

A decontamination device may include an array of one or more individually controllable antimicrobial light segments. Each antimicrobial light segment may include a substrate and one or more light emitting elements, wherein each of the light emitting elements emits light at a wavelength and irradiance sufficient to inactivate one or more microorganisms on a target surface. For example, an antimicrobial light segment may include an LED light strip including a circuit board populated with multiple surface-mounted LEDs including one or more rows arranged in a generally linear pattern. In other examples, an antimicrobial light segment may include a grid of LEDs printed on a solid substrate, panel, or other substrate. The substrate may be rigid or flexible, depending upon the needs of the installation. Other examples may include LED tube lights, light bars, rope lights, bulbs, individual light emitting elements, and any other flexible or inflexible light element configuration or shape. In some examples, the light segments may be customized in size and shape to correspond generally to the dimensions of the common touch surface(s) to be irradiated. In other words, the light segments may be customized such that an entire common touch surface of the common touch object is irradiated simultaneously. In general, the antimicrobial light segments direct light at the wavelength(s) and irradiance at one or more common touch surfaces on the common touch object to achieve a desired level of microbial inactivation at those surfaces, or to reduce or prevent microbial growth at those surfaces, within a desired period of time.

Each individual light element may be directional or omnidirectional. In addition, not all light elements need to have the same directionality; that is, "flood" and "spot" style light elements may be used in the same light segments or through light segments of a lighting array. Individual control of the antimicrobial light segments, or of individual or groups of antimicrobial light source elements within each light segment, may be based on the dimensions of the common touch surface and/or the common touch object, the type of surface or object to be decontaminated, the material of the common touch surface and/or the common touch object, the type of business or environment in which the decontamination is to occur, the type(s) of microorganism(s) to be decontaminated on the common touch surfaces and/or the common touch object, an amount of time expected to be available for decontamination or an amount of time within which decontamination is desired to occur, the distance between the light source elements and the common touch surfaces, the time between decontamination events, the amount of soil residue on the common touch surface(s) and/or other factors that may affect the type and/or amount of antimicrobial light needed to adequately decontaminate the common touch surfaces and/or the common touch object.

The common touch object may include a restaurant menu, airline instruction card, pamphlet, credit card, or other common touch object having a generally flat form factor as described herein, or that can be reduced to a flat form factor. In such an example, the common touch object may include a first common touch surface and an oppositely facing second common touch surface. A decontamination device may include an array of one or more antimicrobial light segments arranged to form a first grid pattern of antimicrobial light source elements sized to irradiate the first common touch surface and arranged to form a second grid pattern or antimicrobial light source elements sized to irradiate the second common touch surface. The antimicrobial light segments may irradiate the first and second common touch surfaces simultaneously. In another example, the antimicrobial light segments may be individually controlled so as to irradiate the first and second common touch surfaces in sequence or in partially overlapping sequences.

Each identified target common touch surface is illuminated with light within one or more antimicrobial wavelength range(s) at a sufficient dosage to effect microbial inactivation on identified target surfaces within a desired period of time. The dosage may be defined as the irradiance, or the energy received by a surface per unit area (e.g., as measured in Joules per square centimeter, $J/cm^{-2}$, $W \cdot s \cdot cm^{-2}$) of the antimicrobial wavelength(s) measured at the target surface. The irradiance is dependent at least in part by the power applied to the light source, the distance from the light source to the target surface, the total surface area illuminated, and the time of exposure.

In some examples, an antimicrobial light treatment protocol for a common touch object may be established depending upon the type of common touch object and/or the environment in which the common touch object is used and/or decontaminated. For example, it may not be necessary to illuminate all zones or surfaces within or on the common touch object continuously or at the same time or at the same dose. Zones can be treated automatically and selectively by the antimicrobial light when the treatment is most effective or most convenient. In a restaurant application, for example, decontamination of menus may be performed between each customer, after each shift, at the end of the day, and/or at any other designated time. In an airline application, for example, decontamination of instruction cards may be performed before/after each flight, during routine cleaning or maintenance, and/or at any other designated time. In another example, the antimicrobial lighting may be manually activated at any time it is determined that the common touch object or common touch surfaces could benefit from an antimicrobial light treatment.

The antimicrobial light treatment protocol may include a high exposure setting (full power on or highest intensity) antimicrobial cycle mode, a treatment interrupt mode (power down) for power savings or to minimize exposure risk. The antimicrobial light treatment protocol may also include a reduced power mode or modified setting in which certain antimicrobial light segments are selectively controlled to output a reduced intensity, but at a level that is sufficient to inactivate one or more microorganisms at the target surface(s). For example, the antimicrobial light elements could be cycled in a "race" mode such that light elements will cycle sequentially throughout the array.

The decontamination devices may include lighting segments or lighting elements that output light within one or more antimicrobial wavelength range(s). For example, some lighting segments or lighting elements may output light within a first antimicrobial wavelength range while other lighting segments or lighting elements output light within a second antimicrobial wavelength range.

An antimicrobial light array may be configured in such a manner that there is overlapping illumination from each successive lighting element at the target surface at which microbial inactivation is desired. This cone of illumination illuminates a surface area dependent upon the design and physical arrangement of the individual light elements in each lighting segment and the distance of the element(s) from the target surface. The design and installation of the light array will be such that there is continuous or intermittent illumination at the surface throughout the target surface being treated. It shall be understood that the irradiance power at the surface being treated is dependent upon the distance between the emitter and the surface. The power of the antimicrobial light shall be controlled such that sufficient irradiance required for microbiological mitigation within the desired time period is achieved. It shall further be understood that the time/irradiance/distance power relationship required for microbiological mitigation depends upon the target organism(s).

LED lifetime of the antimicrobial lighting elements can range from hundreds to in excess of 100,000 hours of operation. Furthermore, the emitted power of the lamp can be modulated using a Pulse-Width-Modulation (PWM) technique to achieve higher irradiant power without stressing the antimicrobial light to the extent that the light's lifetime is adversely affected when operated under constant power. The frequency and duty cycle applied to the antimicrobial light segments may be modulated to achieve the desired irradiance power at the target surface(s). PWM enables the color temperature (spectral distribution) of the LED lamp to be maintained while varying the observed lamp brightness.

Microorganisms that may be found on one or more common touch surface(s) of common touch objects, and that may be inactivated using the decontamination devices and methods of the present disclosure include, but are not limited to, environmental and/or pathogenic microorganisms such as *Listeria monocytogenes, Legionella* sp., *Salmonella* sp., *Pseudomonas* sp., *Acinetobacter* sp., *Moraxella* sp., *Alcaligenes* sp., *Flavobacterium* sp., *Acremonium* sp., *Euro basidium* sp., *Exophiala* sp., *Sporobolomyces* sp., *Rhodotorula* sp., *Campylobacter jejuni, Escherichia coli, Shigella, Vibrio cholerae, C. difficile* and the like, varieties of fungus, algae, mold and/or slime, and/or any other pathogen or microorganism that may be encountered on such common touch surfaces.

FIG. 1 shows a cross-sectional side view of an example decontamination device 10 including one or more antimicrobial light segments for inactivation of one or more microorganisms on common touch surfaces in accordance with the present disclosure. Such microbial inactivation may help to reduce or mitigate the growth of one or more microorganisms on common touch surfaces, improving hygiene of such common touch surfaces and may helping to maintain microbial growth below acceptable levels.

Example decontamination device 10 includes a housing or enclosure 12 formed by a cover 12A, a base 12B and one or more sidewalls 12 defining a decontamination chamber 14. Housing 10 includes an opening or slot 16 in at least one sidewall sized to receive a common touch object 20. Housing 12 may include a door in the at least one sidewall configured to cover slot 16 so as to provide a closed decontamination chamber 14. In this example, common touch object 20 has a generally flat and/or folded form factor and includes at least two common touch surfaces, in this example a first common touch surface 22A and an oppositely facing second common touch surface 22B. Examples of such common touch objects include restaurant menus, instruction cards, pamphlets, etc.

One or more antimicrobial lighting segments 26, in this example antimicrobial lighting segments 26A and 26B, each including one or more light source elements 30, are installed within chamber 14 and are arranged to direct antimicrobial light toward a decontamination area 32. Decontamination area 32 is positioned within chamber 14 and with respect to antimicrobial lighting segments 26A and 26B such that common touch surfaces 22A and 22B are positioned to receive antimicrobial light emitted by antimicrobial lighting segments 26A and 26B, respectively, when common touch object is properly positioned within decontamination area 32.

For example, antimicrobial light segments 26A and 26B may be arranged so as to direct antimicrobial light within one or more antimicrobial wavelength range(s) and having sufficient irradiance to result in inactivation of one or more microorganisms on each of the first and second common touch surfaces 22A and 22B, respectively, within a desired period of time when the common touch object 20 has been received into decontamination area 32. Although a specific number and arrangement of antimicrobial lighting segments 26A and 26N is shown in the example of FIG. 1, it shall be understood that any number of antimicrobial lighting segments 26 may be used, and that any one or more the antimicrobial lighting segments 26 may be installed in alternative locations within the decontamination chamber 14, and that the disclosure is not limited in this respect.

In some examples, some or all of antimicrobial lighting segments 26 may be implemented as a grid or array of LED lighting elements 30 surface mounted to a rigid or flexible substrate, such as a circuit board. The grid or array of LED lighting elements 30 may be arranged to direct antimicrobial light of sufficient irradiance (power received by a target surface per unit area) of these wavelengths to result in inactivation of one or more microorganisms at the target surface(s) within a desired period of time. In other examples, antimicrobial lighting segments 26A and 26B may be implemented using flexible LED light strips. As such, each antimicrobial lighting segment 26 may be cut and/or shaped to fit a target space within housing where the segment is to be installed or to form one or more lighting segment(s) having the desired size, shape and/or number of light source elements 30. In other examples, some or all of antimicrobial lighting segments 26 could be LED tube lights, light bars, rope lights, bulbs, individual light source elements, and any other flexible or rigid light element configuration or shape. The light source elements 30 may be LEDs or may be any other light source capable of emitting antimicrobial light as described herein.

In some examples, the antimicrobial lighting elements 30 are configured to emit light normal to the plane of the substrate. In other examples, some of the lighting elements may be mounted in a staggered arrangement such that a first subset of the light source elements 30 are mounted or configured to emit light normal to the substrate (and thus normal to the plane of the decontamination area 32 and/or the high touch object 20), the second subset of the light source elements 30 are mounted or configured to emit light at a predetermined angle from the normal to the substrate (e.g., 15 degrees, 30 degrees, etc.). Alternating rows of lighting elements on the substrate may follow an offset pattern. Such an arrangement may eliminate any shadowing effect for high touch objects with 3-dimensional surfaces that may result if all lighting elements emit light in the same direction toward the high touch object.

Decontamination device 10 is further configured to automatically draw or feed common touch object 20 through slot 16 and into decontamination area 32. For example, decontamination device may include one or more feed rollers 28A and/or 28B configured to draw common touch object 20 through slot 16 in the direction indicated by arrow A and into chamber 14 and decontamination area 32. Decontamination device 10 may further include one or more guides or rails 24 by which common touch object 20 is guided into decontamination area 32 for receipt of the antimicrobial light treatment. Decontamination area 32 may further include a holder or tray configured to receive and hold common touch object 20 in place during receipt of the antimicrobial light treatment.

In use, a user feeds a first end of the common touch object 20 into slot 16 in the direction indicated by arrow A. Common touch object 20 is picked up by feed rollers 28A and/or 28B, which draw common touch article 20 into chamber 14 and until it is positioned within decontamination area 32. Antibacterial light segments 26A and/or 26B may be manually activated by the user or may be automatically activated upon detecting presence of common touch object 20 in position decontamination area 32. Once common touch object 20 has been exposed to the antimicrobial light for a defined period of time, the antimicrobial lights are deactivated and the common touch object may be automatically ejected back through slot 16 in the direction as indicated by arrow B. In another example, the article may drop into a holding bin and be irradiated with one or more wavelengths of antimicrobial light to maintain an antimicrobial effect. The power level in that example may be a maintenance dose.

Commonly touched environmental surfaces have been linked to the transmission of pathogens from one person to another through cross-contamination. Microorganisms that may be found on one or more common touch surface(s) of common touch objects, and that may be inactivated using the decontamination devices and methods of the present disclosure include, but are not limited to, environmental and/or pathogenic microorganisms such as *Listeria monocytogenes, Legionella* sp., *Salmonella* sp., *Pseudomonas* sp., *Acinetobacter* sp., *Moraxella* sp., *Alcaligenes* sp., *Flavobacterium* sp., *Acremonium* sp., *Euro basidium* sp., *Exophiala* sp., *Sporobolomyces* sp., *Rhodotorula* sp., *Campylobacter jejuni, Escherichia coli, Shigella, Vibrio cholerae, C. difficile* and the like, varieties of fungus, algae, mold and/or slime, and/or any other pathogen or microorganism that may be encountered on such common touch surfaces. Application of the antimicrobial light to inactivate one or more microorganisms on common touch surfaces may help reduce the probability of transmission of microorganisms through cross-contamination of the common touch surfaces.

Each antimicrobial light segment 26 may be individually controllable such that they may be activated and/or deactivated independently of one another. In addition or alternatively, each light source element within each antimicrobial light segment 26 may also be individually controllable such that they may be activated and/or deactivated independently of one another. Antimicrobial light segments 26 emit antimicrobial light within at least one antimicrobial wavelength range and having irradiance sufficient to inactivate one or more microorganisms at the target surface(s) (that is, one or more common touch surfaces 22) within a specified period of time. For example, one or more of antimicrobial light segments 26 may include one or more light source elements that emit antimicrobial light within a first wavelength range of 380-420 nm and having an irradiance sufficient to inactivate one or more microorganisms at the target surface(s) within a specified period of time. In some examples, the light within the first wavelength range has a peak wavelength of about 405 nm. As another example, one or more of antimicrobial light segments 26 may include one or more light source elements that emit antimicrobial light within a second wavelength range, wherein the second wavelength range may include ultraviolet A (UVA) light within a wavelength range of 315-400 nm, ultraviolet B (UVB) light within a wavelength range of 280-315 nm and/or ultraviolet C (UVC) light within a wavelength range of 200-280 nm and having an irradiance sufficient to inactivate one or more microorganisms at the target surface(s) within a specified period of time.

Use of multiple customizable and individually controllable antimicrobial light segments 26 allows for greater distribution and illumination of antimicrobial light to achieve microbial inactivation on common touch surfaces of any dimension, size or shape. In addition, for examples where the common touch object does not have a flat form factor, one or more antimicrobial light segments may be placed so as to surround a three-dimensional object, and so to direct antimicrobial light toward any desired surface of such three-dimensional objects. For example, the common touch objects may include 3D objects with a low profile or small depth dimension relative to length and width, such puck-shape or disk-shaped objects. The antimicrobial lighting array may include multiple angles of illumination to minimize shadowing. Areas or surfaces that may be shadowed from one antimicrobial light source may be illuminated by other antimicrobial light sources strategically placed in and around the interior of decontamination chamber 14 such that shadowing can be minimized.

It shall be understood that other configurations of antimicrobial light arrays including one or more antimicrobial light segments may be adapted for installation into decontamination chamber 14, and any type of lighting segment(s) capable of emitting one or more antimicrobial wavelengths may be used. In addition, multiple rigid and/or flexible antimicrobial light segments may be cut, bent, or curved to fit almost any flat, planar, curved or any other shape may be assembled together in an array of individually controllable antimicrobial light segments to provide thorough antimicrobial light application to any common touch surface where growth of microorganisms is a concern.

Figure 2A:
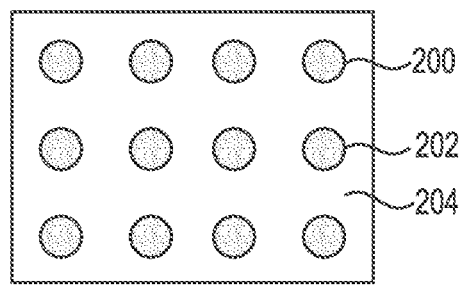
FIGS. 2A and 2B show example grid designs for an antimicrobial light segment.
Figure 2B:
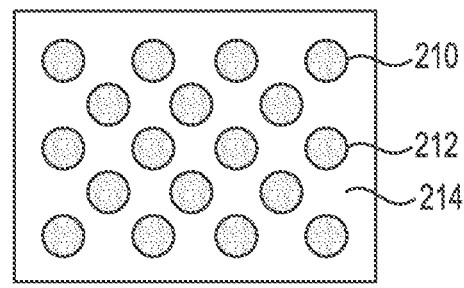

FIGS. 2A and 2B show example antimicrobial light segments 200 and 210, respectively. Each antimicrobial light segment 200, 210 includes a plurality of light source elements 202, 212, arranged in a grid pattern on a substrate 204, 214. The light source elements may be configured in a grid design of suitable dimensions (e.g., length, width, diameter, etc., depending upon the shape) and grid density (the number of light source elements per unit area) to provide sufficient irradiance to achieve inactivation of one or more microorganisms on a target surface within a desired period of time. For example, the grid pattern may be configured to have dimensions and grid density corresponding to the dimensions of the target surface(s) to be irradiated. As one example, a first antimicrobial lighting segment such as antimicrobial light segment 200 and/or 210 may be configured to direct light at first common touch surface 22A of common touch object 20 and a second antimicrobial lighting segment such as antimicrobial lighting segment 200 and/or 210 may be configured to direct light at second common touch surface 22B of common touch object 20.

Antimicrobial light segment 200 includes a plurality of light source elements, such as light source element 202, arranged in a stacked grid design where each row of light source elements is arranged in line with the light source elements of the adjacent rows. Antimicrobial light segment 210 includes a plurality of light source elements, such as light source element 212, arranged in an offset grid design where each row of light source elements is offset from the light source elements of the adjacent rows. In some examples, an offset grid design such as antimicrobial light segment 210 may enable the light source elements to be packed closer together, thus increasing the density of the light source elements on the substrate. By increasing the density of the light source elements, the amount of light energy impinging on the target surface may be increased. It shall be understood that any suitable arrangement of light source elements on a substrate may be used, and that the disclosure is not limited in this respect.

Figure 2C:
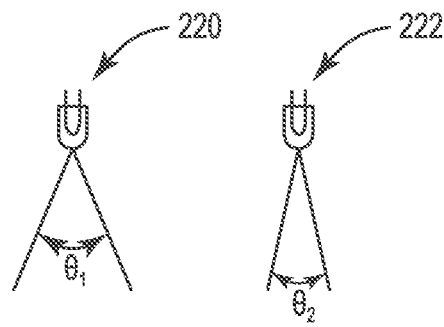
FIG. 2C shows example emission angles for two different LED light source elements.

Light source elements, such as LEDs, are designed to emit light at a known emission angle. The angle is defined as the angle at which the light intensity is 50%. Designing a grid of light source elements based on the emission angle allows the energy impinging upon the target surface to be maximized, for example, when overlapping emission profiles of neighboring elements increase the intensity. FIG. 2C shows two representative emissions angles for a first light source element 220 and a second light source element 222.

In FIG. 2C, the emission angle of light source element 220, $\theta_1$ is relatively greater than the emission angle of light source element 222, $\theta_2$. As a result, in order to achieve overlapping emission, LEDs having a wider emission angle (such as light source element 220) can be relatively further apartment as compared to light source elements having a smaller emission angle (such as light source element 222). The distance between the light source elements and the target surface also affects the emission overlap. These parameters (the emission angle of the light source elements, the distance between the light source elements and/or the density of the light source elements, the distance to the target surface, etc.) can be tailored to maximize the antimicrobial light energy impinging at the target surface. Alternatively, the dimensions can be tailored to achieve a desired amount of antimicrobial light energy impinging at the target surface.

Figure 3:
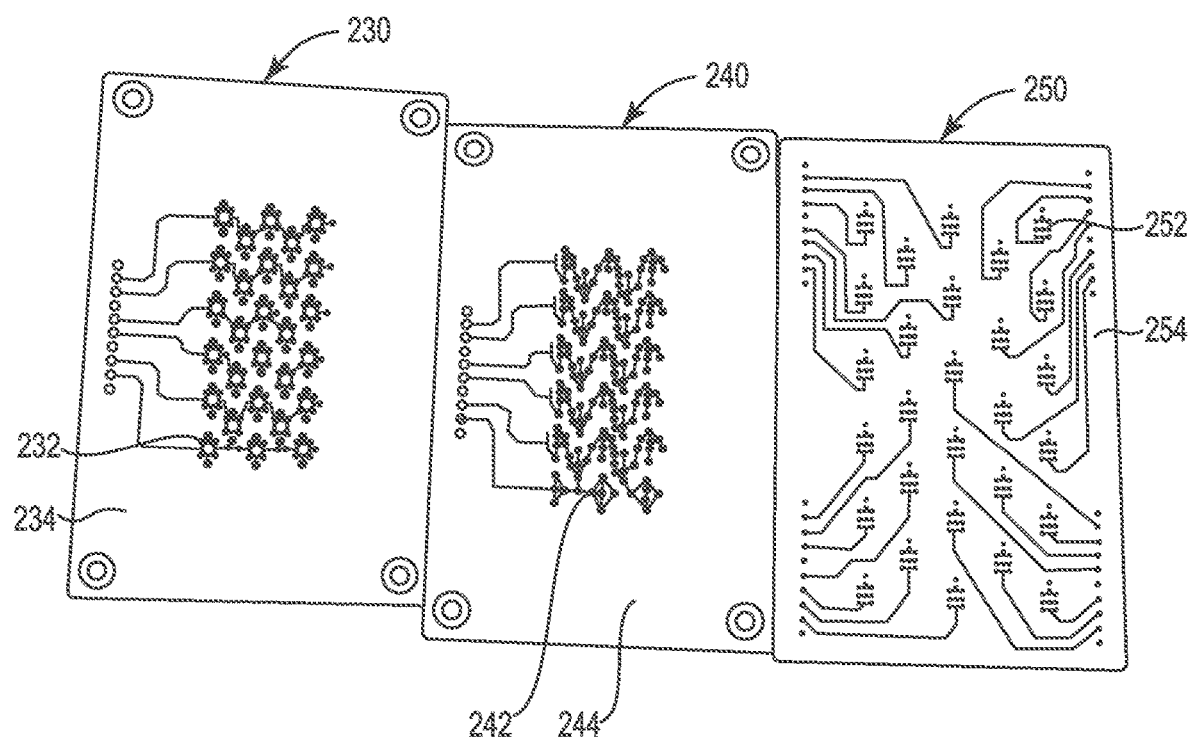
FIG. 3 is a photograph showing two example antimicrobial light segments, each including a plurality of antimicrobial light source elements arranged in a grid pattern on a substrate.

FIG. 3 is a photograph showing two example antimicrobial light segments 230 and 250. Each antimicrobial light segment 230, 250 includes a plurality of antimicrobial light source elements arranged in a grid pattern on a substrate 234, 254, respectively. Circuit board 240 shows the unpopulated circuit board layout of segment 230. In these examples, each antimicrobial light segment includes 28 LED antimicrobial light source elements. Antimicrobial light segment 230/240 has a nominal 0.333-inch spacing and is populated with surface mounted LED light source elements, such as light source element 232. Antimicrobial light segment 250 has a nominal 0.5-inch spacing layout. In these examples, the dimensions of the substrates 234/244, 254 are the same, but the increased distance between light source elements in segment 250 results in a decreased density of light source elements in segment 250 as compared to segment 230/240.

Figure 4:
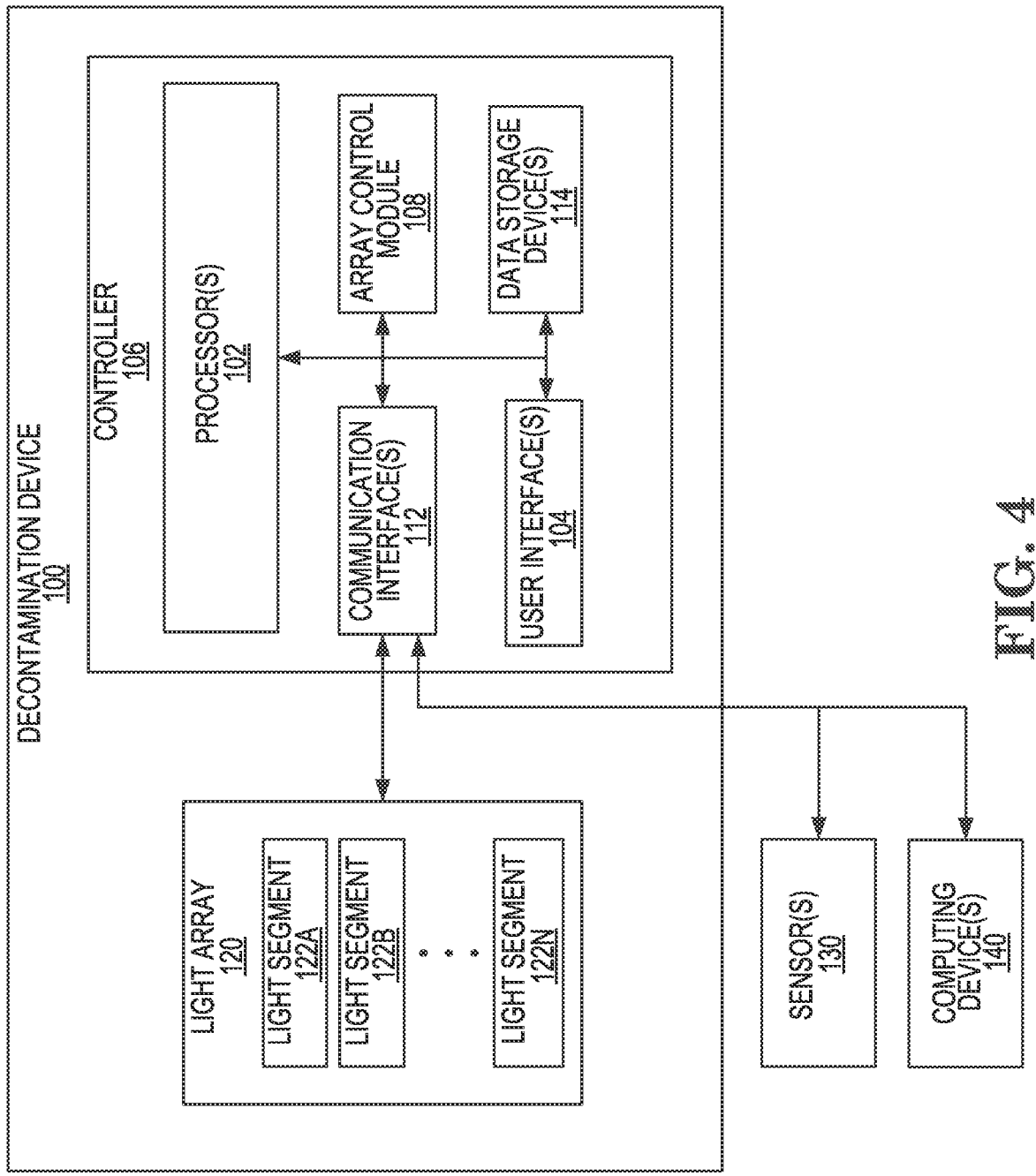
FIG. 4 is a block diagram illustrating an example decontamination device including a light array, a controller and one or more individually controllable antimicrobial light segments in accordance with the present disclosure.

FIG. 4 is a block diagram illustrating an example decontamination device 100 for inactivation of one or more microorganisms on common touch surfaces. Decontamination device 100 includes a controller 106 and a light array 120 including one or more antimicrobial light segments 122A-122N. Antimicrobial light segments 122A-122N may include any number of segments, and it shall be understood that the disclosure is not limited in this respect. In some examples, antimicrobial light segments 122A-1122N are individually controllable. Device 100 may further include one or more sensor(s) 130.

In some examples, each antimicrobial light segment 122A-122N may be implemented using a commercially available LED light strip that emits light within a first antimicrobial wavelength range of 380-420 nm and having a peak wavelength of about 405±5 nm, such as the Single Color Outdoor Weatherproof LED Flexible Light Strip, wavelength 405 nm, Part Number WFLS-UV30, available from Super Bright LEDs Inc., of St. Louis, Missouri, USA (www.superbrightleds.com). These segments are waterproof, flexible, and may be cut and/or bent to desired lengths or shapes for each application. In some examples, each antimicrobial light segment 122A-122N may be adhered to a mounting fixture using an integrated adhesive strip. In other examples, each antimicrobial light segment 122A-122N may be affixed to the desired location using a suitable adhesive or mounting hardware. In some examples, one or more of antimicrobial light segments 122A-122N may be implemented using a plurality of light source elements arranged in a grid on a rigid or flexible substrate, such as shown in FIGS. 2A-2C.

Decontamination device 100 further includes one or more processors 102, an array control module 108, one or more user interface components 104, one or more communication components 112, and one or more data storage components 114. User interface components 104 may include one or more of audio interface(s), visual interface(s), and touch-based interface components, including a touch screen, display, speakers, buttons, keypad, stylus, mouse, or other mechanism that allows a person to interact with and/or control decontamination device 100. In this example, communication components 112 are configured to communicate control signals from processors 102 in accordance with instructions stored in array control module 108 and/or received via the user interface 104 to control antimicrobial light segments 122A-122N within antimicrobial lighting array 120. The antimicrobial light segments 122A-122N may be controlled individually or collectively. Communication components 112 are also configured to allow controller 106 to communicate with other remote or local computing devices 135 via wired and/or wireless connections. For example, the remote or local computing devices 135 may include a smart phone, tablet, laptop or other mobile computing device, or a central computing device. In this way, control of the decontamination device 100 may be accomplished through computing device(s) 140.

Array control module 108 includes computer readable instructions configured to be executed on the one or more processors 102 to enable controller 106 to control activation of antimicrobial light segments 122A-122N of light array 120. The antimicrobial light segments 122A-122N may be controlled individually or collectively. For example, array control module 108 may enable controller 100 to control activation of one or more antimicrobial light segments 122A-122N based on status information signals or commands received from user interface 112. In another example, array control module 108 may enable controller 100 to control activation of one or more antimicrobial light segments 122A-122N based on status information signals or commands received from any one of computing device(s) 140. In another example, control module 108 may enable controller 100 to control activation of one or more antimicrobial light segments 122A-122N based on the signals received from one or more sensors 130.

In some examples, one or more of the antimicrobial light segments 122A-122N may be activated to emit antimicrobial light at a first, high setting (that is, a highest intensity). As another example, one or more of the antimicrobial light segments 122A-122N may be activated to emit antimicrobial light at a second, low setting (that is, relatively lower intensity than the high setting). As another example, one or more of the antimicrobial light segments 122A-122N may be deactivated so as not to emit antimicrobial light, or be placed in an "off" setting, or a sleep mode. It shall be understood, therefore, that each of the antimicrobial light segments 122A-122N may be controlled by controller 106 to individually active/deactivate and/or adjust the power and/or intensity of the antimicrobial light output by each antimicrobial light segment 122A-122N, and thus to adjust the irradiance of the antimicrobial light received at the target surface(s).

In other examples, the antimicrobial light segments 122A-122N may be controlled by controller 106 such that one or more of the antimicrobial light segments 122A-122N emit light within a first antimicrobial wavelength range, one or more of the antimicrobial light segments 122A-122N emit light within a second antimicrobial wavelength range, and/or one or more of the antimicrobial light segments 122A-122N are deactivated or turned off. It shall be understood, therefore, that each of the antimicrobial light segments 122A-122N may be individually controlled to control or adjust the wavelength of the antimicrobial light output by decontamination device 100, and thus to adjust the wavelength(s) of antimicrobial light received at the target surface(s).

In some examples, light within the first antimicrobial wavelength range includes light within a wavelength range of about 380-420 nm. The light emitted within the first antimicrobial wavelength range may include a peak wavelength of about 405 nm. In some examples, light within the second antimicrobial wavelength range may include ultraviolet A (UVA) light within a wavelength range of 315-400 nm, ultraviolet B (UVB) light within a wavelength range of 280-315 nm and/or ultraviolet C (UVC) light within a wavelength range of 200-280 nm.

Data storage devices 114 of controller 106 include data received, used or generated by processors 102 during execution of the array control module 108 and/or other functionality of controller 106. For example, storage components 114 may include any data or cycle signals received from sensors 130, data entered by a user via user interface components 104, data used or generated by array control module 108, or data or commands received from computing device(s) 140.

Decontamination device 100 (including controller 106 and antimicrobial light segments 122A-122N) may include its own internal power supply (such as one or more batteries), or it may be powered from line power (e.g., AC power), such as through a wall outlet.

Antimicrobial light segments 122A-122N may also include one or more LED drivers that are connected to controller 106 through communication interface(s) 112, and which are configured to drive the antimicrobial light segments 122A-122N in response to commands received from controller 106.

Array control module 108 may include instructions that enable controller 106 to control antimicrobial light segments 122A-122N using one or more settings. The antimicrobial light segments 122A-122N may be controlled individually or collectively For example, the settings may include a high or full power or level setting (e.g., a maximum voltage/current applied), which means that maximum power or level is applied to a selected one or more of the antimicrobial segments 122A-122N. The settings may also include one or more modified power or level settings, such as one or more dimmed settings (e.g., 50% of maximum power, 25% of maximum power, or other selected percentage(s)), which means that the modified power is applied to selected one or more of the antimicrobial light segments. The settings may also include a deactivated setting, in which one or more of the antimicrobial light segments 122A-122N are turned off or placed in a sleep mode.

The different level settings correspond to different levels of light output by the antimicrobial light segments 122A-122N. For example, a high or maximum setting corresponds to the highest light output of an antimicrobial light segment (however that maximum may be defined for the system design). A medium or modified setting corresponds to a reduced light output (reduced or lower relative to the high or maximum setting) of an antimicrobial light segment. An "off" setting corresponds to no light output. The medium or modified settings do not necessarily correspond in a linear relationship with the current applied to an antimicrobial light segment, as the response curve of the antimicrobial lights are not necessarily linear with respect to the applied current. In other words, a 50% power applied (compared to a maximum power) does not necessarily result in 50% of maximum light output if the response of the antimicrobial light in questions is not linear. However, it shall be understood that reduced settings correspond to reduced power or voltage applied, and a reduced light output by the affected antimicrobial light segments.

In some examples, antimicrobial light segments 122A-122N may be individually controllable by array controller 106 such that they are not all necessarily driven at the same setting(s) at the same time(s). Thus, at any given time, a first selected set of one or more antimicrobial light segment(s) 122A-122N may be driven at first, high, setting, a second selected set of one or more antimicrobial light segment(s) 122A-122N may be driven at a second, modified, setting, and a third selected set of one or more antimicrobial light segment(s) 122A-122N may be deactivated or off.

Decontamination device 100 may further include one or more sensor(s) 130. Sensor(s) 130 may include, for example, one or more optical sensors that detect presence of one or more wavelengths emitted within decontamination chamber 14 and/or detect the irradiance (optical power) received at one or more of the target surfaces. One or more of sensor(s) 130 may detect light within the first wavelength range, and/or light within the second wavelength range. For example, sensor(s) 130 may include one or more photodetectors that detect antimicrobial light within the first wavelength range and/or one or more photodetectors that detect light within the second antimicrobial wavelength range. The one or more sensor(s) 130 may generate signal(s) corresponding to the presence of light within the relevant wavelengths or the irradiance of the relevant wavelengths. The photodetectors may be positioned within decontamination chamber so as to measure irradiance of antimicrobial wavelengths received at a target surface or that may be representative of the irradiance of the antimicrobial wavelengths received at a target surface. For example, one or more photodetectors may be positioned in or near decontamination area 32 so as to receive an irradiance representative of that which would be received by a target surface being subjected to an antimicrobial light treatment within decontamination chamber 14.

Sensor(s) 130 may further include one or more sensors that detect presence of a common touch object 12. For example, one or more sensors may be positioned at or near the entrance 16 to decontamination device 10 so as to detect when a common touch object enters the decontamination chamber 14. As another example, one or more sensors may be positioned at or near decontamination area 32 to detect when a common touch object is properly positioned within the decontamination area 32. As another example, one or more sensors may detect whether a door to the decontamination device is open or closed. Sensor(s) 130 may also include one or more temperature sensors to monitor the temperature of the objects or within the decontamination chamber to help ensure that the objects being decontaminated do not get too warm.

Decontamination device 100 may be controlled through user interface 104 in response to inputs from a user. For example, the user interface may include an on/off switch, button, or selector by which a user powers on device 100. User interface 104 may also include one or more controls for activating the one or more antimicrobial lighting segments 122A-122N. For example, through the user interface 104, a user may input the desired settings (e.g., high, modified, off, etc.) for some or all of the antimicrobial light segments 122A-122N. As another example, a user my input information regarding the type of common touch article and/or common touch surface to be decontaminated and controller 106 may determine how to control the antimicrobial light segments 122A-122N based on the received information. The controller may automatically determine which antimicrobial wavelengths should be emitted, which of the one or more antimicrobial light segments 122A-122N should be activated, power setting(s) for each antimicrobial light segment 122A-122N to be activated, the amount of time to apply the antimicrobial light, and any other parameter relevant to the dosage of antimicrobial light to be delivered, based on the type of common touch object and/or common touch surface to be decontaminated.

For example, in a restaurant setting, staff may manually activate and/or control decontamination device to apply antimicrobial light treatment to articles such as menus and/or other common touch objects having common touch surfaces. The decontamination device 100 may be set up at, for example, a host/hostess station or other designated location within the restaurant. Menus may be cleaned between each customer, during/after each shift, or any other time decontamination is deemed necessary or desirable. As another example, a service technician or custodian may manually activate and/or control decontamination device during a service call. As another example, a user may manually activate and/or control decontamination device 100 remotely via one or more of computing device(s) 140.

Figure 5:
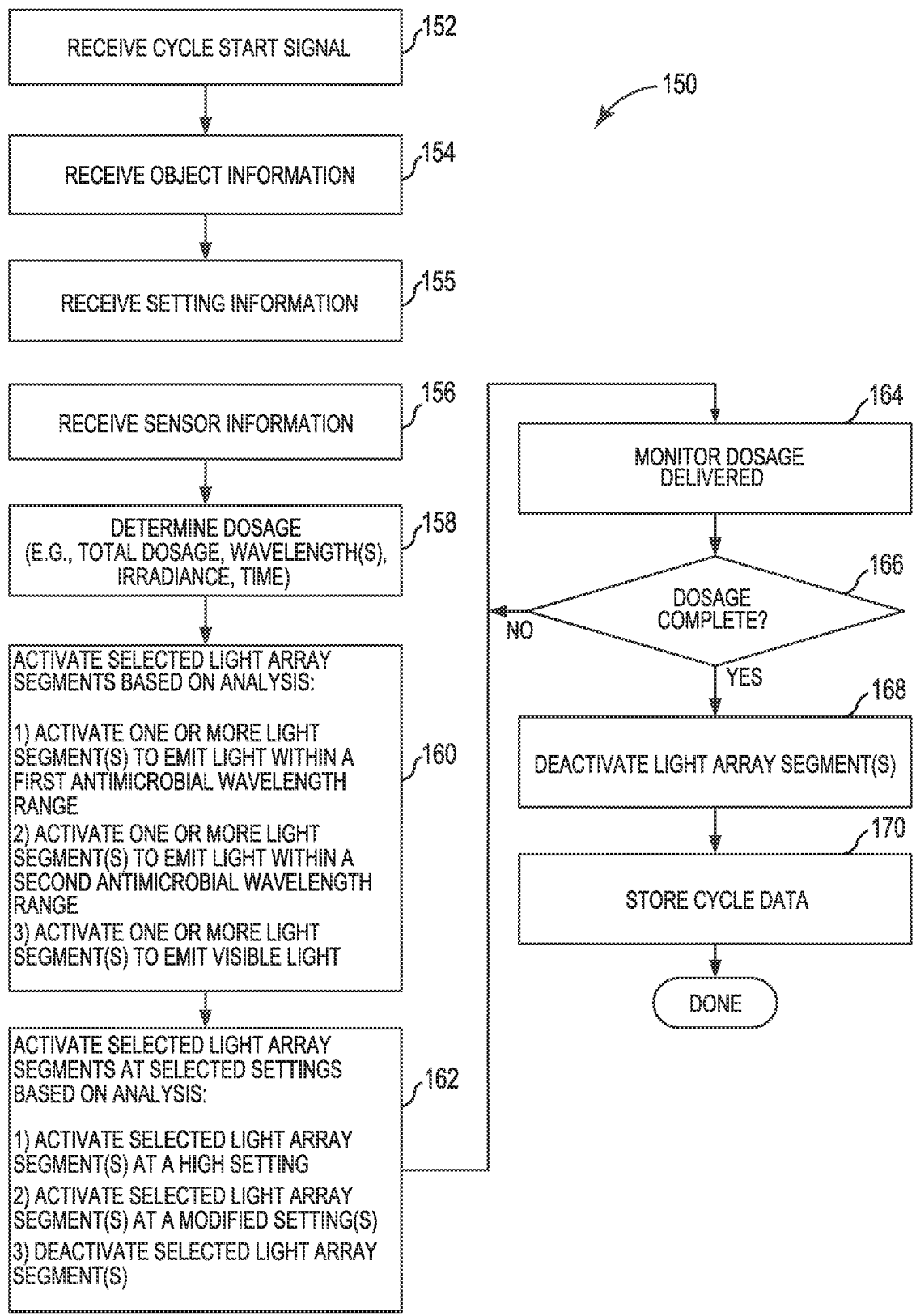
FIG. 5 is a flowchart illustrating an example process by which a controller may individually control one or more antimicrobial light segments for microbial inactivation on common touch surfaces in accordance with the present disclosure.

FIG. 5 is a flowchart illustrating an example process 150 by which a computing device, such as controller 106 of FIG. 4, may control one or more antimicrobial light segments, such as antimicrobial light segments 122A-122N of FIG. 4, of a decontamination device in accordance with the present disclosure. Process (150) will be described with respect to application and control of antimicrobial light to achieve microbial inactivation of one or more microorganisms at one or more common touch surfaces of a common touch object having a generally flat or folded form factor; however, it shall be understood that process (150) may apply to application and control of antimicrobial light for microbial inactivation at one or more common touch surfaces of common touch objects of any size and shape, including three-dimensional objects, and that the disclosure is not limited in this respect.

In the example of FIG. 5, a computing device (such as controller 106 of FIG. 3) receives a cycle activation signal (152). The cycle activation signal may include a signal generated in response to input from a user, such as depressing an on/off or start switch, selecting an on/off or start button on a touch screen, or other user actuatable means by which the user may initiate an antimicrobial lighting treatment. As another example, cycle activation signal may be automatically received from one or more sensors (such as sensors 130 in FIG. 4) upon detecting presence of a common touch object in the decontamination area 32 of decontamination device 10.

In response to receipt of the activation signal, the computing device obtains information needed to determine the dosage of antimicrobial light to be applied by the antimicrobial lighting segments to the common touch surfaces within the decontamination area (154, 155, 156). For example, the computing device may receive object information indicative of one or more characteristics of the common touch object that may affect the dosage of antimicrobial light to be applied (154). The object information may include, for example, an object type (e.g., menu, instruction card, etc.), a material type (e.g., plastic, paper, laminate, etc.), or other relevant object information. The object information may be manually input by a user via a user interface, such as user interface 104. For example, the user interface may present one or more object information options from which a user may select the object information corresponding to the common touch object. Alternatively, the decontamination device may operate on a default setting in which no object or setting information is received.

As another example, the computing device may receive setting information indicative of one or more settings related to the dosage of antimicrobial light to be applied (155). For example, the user interface may present one or more user selectable settings from which a user may select a desired setting for the decontamination device. The settings may correspond to different dosage levels of antimicrobial light to be applied to the objects within the decontamination area (e.g., high, medium, low, etc.). As another example, the settings may correspond to different predetermined durations of the decontamination cycle (regular cycle, extended cycle, quick cycle, etc.). The irradiance and/or wavelengths of the antimicrobial light emitted for each durational setting may be automatically by the adjusted such that sufficient inactivation of one or more microorganisms on the target common touch surface(s) is achieved within the selected cycle duration.

The computing device may also receive information from one or more sensors associated with the decontamination device (156). For example, the computing device may receive information from one or more sensors indicative of whether the common touch object is properly positioned within the decontamination area. In this way, the computing device may help to ensure that the entirety of the common touch surface(s) are in a position to receive an effective dose of the antimicrobial lighting treatment.

As another example, the computing device may receive dimensional information from one or more sensors indicative of the size and/or shape of the common touch object and/or the common touch surface(s) within the decontamination area. For example, the computing device may determine the dimensions (e.g., length, width, etc.) of the common touch object and/or common touch surface(s) based on information received from one or more sensors. Based on the dimensional information received from the one or more sensors, the computing device may control the antimicrobial lighting segments such that only those antimicrobial lighting segments directing light corresponding to the dimensions of the common touch object and/or the common surfaces are activated during the antimicrobial lighting treatment. This may help to save power and/or extend the lifetime of the lighting elements within the antimicrobial lighting array.

The computing device determines the dosage of the antimicrobial light to be applied by the antimicrobial lighting array (158). The dosage is determined by the wavelength(s), irradiance, and amount of time (duration) that the antimicrobial light is to be applied. In some examples, the dosage is a default dosage that is automatically applied during each decontamination cycle. In other examples, the dosage may be determined based on a selected dosage level input by a user via a user interface. In other examples, the dosage may be determined based at least in part on received object information (such as the object type and/or material type described above). In other examples, the dosage may be determined based at least in part on received setting information input by a user. In other examples, the dosage may be determined based at least in part on sensor information (such as the position and/or dimensional information described above).

In some examples, in order to determine a dosage effective to inactivate one or more microorganisms on the common touch surface(s) (158), the computing device determines the antimicrobial wavelength(s), irradiance, and amount of time (duration) for the antimicrobial light treatment. For example, the computing device may determine that the dosage includes antimicrobial light within a first antimicrobial wavelength range of 380-420 nanometers (nm), and/or antimicrobial light within a second antimicrobial wavelength range, such as ultraviolet light within a wavelength range of 10-400 nanometers (nm). In some examples, the antimicrobial light within the first wavelength range has a peak wavelength of about 405 nm. In some examples, the antimicrobial light within the second wavelength range may include ultraviolet A (UVA) light within a wavelength range of 315-400 nm, ultraviolet B (UVB) light within a wavelength range of 280-315 nm and/or ultraviolet C (UVC) light within a wavelength range of 200-280 nm. In some examples, the computing device may determine the dosage of the antimicrobial light based on the object information, the setting information, and/or the sensor information. In other examples, the computing device does not receive any of object information, setting information, or sensor information, and in those examples, the computing device may use a default dosage. Based on the one or more antimicrobial wavelength(s) to be applied, the computing device determines the irradiance to be emitted by each selected antimicrobial lighting setting and the duration that each selected antimicrobial lighting segment is to be activated.

The computing device activates selected ones of the one or more antimicrobial light segments in such a way as to apply the determined dosage of antimicrobial light to the common touch surfaces within the decontamination area (160). For example, the computing device may activate one or more light segments that emit light within a first antimicrobial wavelength range and/or activate one or more light segments that emit light within a second antimicrobial wavelength range. As another example, the computing device may determine that some or all of the antimicrobial light segments should be activated at a high or maximum setting; the computing device may determine that some or all of the antimicrobial light segments should be activated at a modified or reduce setting(s); and/or the computing device may determine that some or all of the light segments should be deactivated (162).

The computing device activates the selected ones of the antimicrobial light segments at the determined wavelengths at the determined irradiance for the determined amount of time in order to apply a dosage effective to inactivate one or more microorganisms at the target common touch surfaces within the decontamination area.

During the antimicrobial lighting treatment, the computing device may monitor the dosage delivered (164) at the common touch surfaces by the antimicrobial lighting array. In one example, the computing device keeps track of the duration of the antimicrobial light treatment. If the predetermined amount of time has not elapsed, the computing device determines that the dosage is not complete (NO branch of 166), and the computing device continues to control antimicrobial lighting segments to deliver the determined antimicrobial lighting treatment until the predetermined time has elapsed. Once a predetermined amount of time has elapsed, the computing device determines that the dosage is complete (YES, branch of 166), and deactivates the selected antimicrobial light segments (168).

In another example, decontamination device includes one or more sensors that measure the irradiance received in the decontamination area and/or emitted by the selected antimicrobial light array segments. For example, one or more photodetectors may measure an irradiance of antimicrobial light received at a representative surface and/or an irradiance of light emitted by the one or more antimicrobial light segments. The computing device may determine the dosage delivered based on the detected irradiance and the amount of time the antimicrobial light has been applied. If the target dosage has not been received (NO branch of 166), the computing device continues to control antimicrobial light segments to deliver the determined antimicrobial lighting treatment. Once the target dosage has been achieved (YES branch of 166), the computing device deactivates the selected antimicrobial light segments (168).

The computing device may also include one or more storage device(s) in which to store cycle data (168). The cycle data may include, for example, details concerning the antimicrobial light applied during each decontamination cycle, such as total dosage delivered during the decontamination cycle, the antimicrobial wavelength(s) applied, the irradiance of each of the antimicrobial wavelength(s), and the duration that each of the antimicrobial wavelength(s) were applied. The cycle data may further include information concerning which light segments of the antimicrobial lighting array were activated during the antimicrobial lighting treatment and the irradiance and duration corresponding to each. The cycle data may further include a time/date stamp, a decontamination device id, a location id/facility name, as well as any received object information, setting information and/or sensor information. It shall be understood that the cycle data may include other information relevant to the antimicrobial lighting treatment, and that the disclosure is not limited in this respect.

In some examples, the computing device may further control decontamination device to automatically eject the common touch object from the decontamination chamber once the determined dosage has been delivered and the selected light array segments have been deactivated (168).

Figure 6:
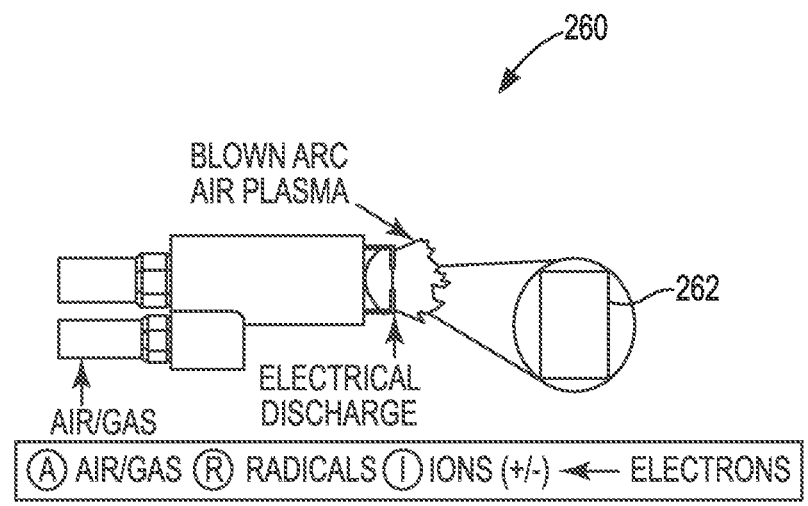
FIG. 6 shows a block diagram of an example decontamination device including a non-thermal (NT) plasma generator for inactivation of one or more microorganisms on common touch surfaces in accordance with the present disclosure.

FIG. 6 shows a block diagram of an example decontamination device 260 including a non-thermal (NT) plasma generator for inactivation of one or more microorganisms on common touch surfaces, such as common touch surface 262, in accordance with the present disclosure. Nonthermal plasmas, also known as atmospheric cold plasmas, can be generated by passing air or a feed stream of gas such as nitrogen, helium, oxygen or other gases mixtures through a high voltage electric field resulting in the creation of a dynamic gaseous state of highly energetic and highly reactive species such as hydroxy radicals, nitroxy radicals, ozone, ions, electrons and other excited atoms. These energetic gaseous species can immediately react with various microbial species on a material surface causing microbial inactivation. Experimental results on plastic coupons (Delrin) inoculated with model biocontaminants have shown positive kill rates when coupons were exposed to a cold air plasma discharge at a distance of approximately 1.0 inch from the plasma source as shown in the following table:

| Species | Type | Exposure Time | Log Reduction |
|---|---|---|---|
| Staph aureus | Gram + | 30 sec | >6 log |
| P. aeruginosa | Gram − | 30 sec | >6 log |
| B. subtilis | Spore | 60 sec | >3 log |

The process of microbial decontamination can occur in a closed container designed to hold common touch objects, such as flat or folded articles (e.g., restaurant menus, safety instructions or similar instructions for use (IFUs)) made from a wide variety of materials of construction. By applying a plasma discharge device to the containment space, energetic gas species will form, fill the space and permeate throughout as well as between the layers, folds, pages, of the common touch object, effecting disinfection through microbial inactivation on all surfaces. This can be accomplished safely and without adversely affecting the physical or visual quality of the common touch objects.

In a similar manner, disinfecting agents creating a fog, gaseous cloud or penetrating vapor within a decontamination chamber may inactivate one or more microorganisms on common touch objects occupying space in the decontamination chamber. Chlorine dioxide (ClO2) sachet is an example of a form of biocide agent contained in a pouch or packet, that when placed in the decontamination chamber, can release biocidal gas to fill the space of the enclosure and cause microbial inactivation of one or more microorganisms given adequate time at proper concentrations of chlorine dioxide. For example, ClO2 gas released from a PET pouch placed in closed shipping containers of fruit and vegetables can inactivate E. coli and other harmful pathogens on produce surfaces within the container. Similarly, ClO2 gas, released in a controlled manner from a semi-permeable membrane such as PET, can inactivate harmful pathogens contaminating surfaces on articles such as menus, instructions, and other flat stock materials.

Figure 7:
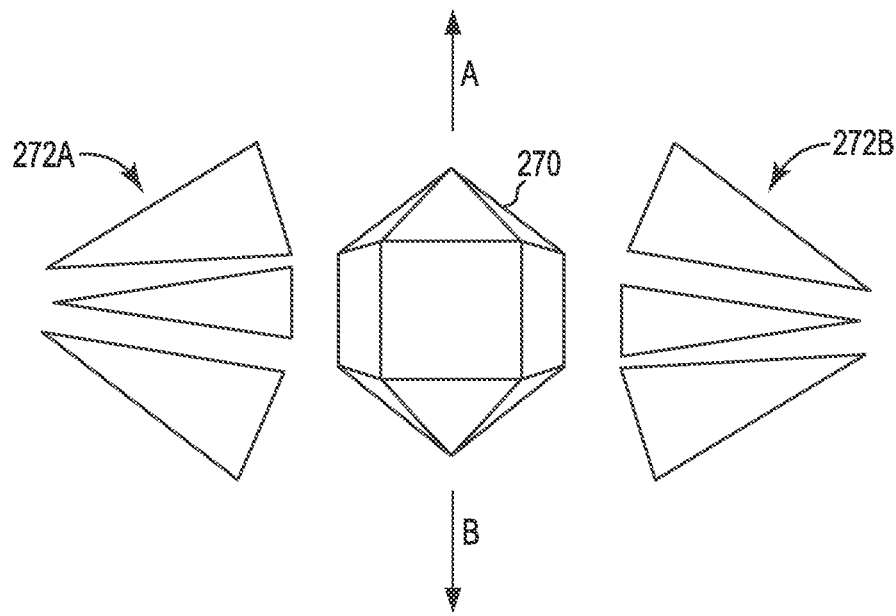
FIG. 7 shows a schematic diagram of one or more antimicrobial lighting segments for decontamination of a three-dimensional object.

FIG. 7 shows a schematic diagram of one or more antimicrobial lighting segments 272A, 272B, for decontamination of a three-dimensional object 270. A decontamination device for decontaminating a three-dimensional object may further include additional antimicrobial lighting segments that are not shown in FIG. 7 for purposes of clarity. For example, additional lighting segments may be included to irradiate object 270 from a top side and a bottom side, as well as from left side (272A) and right side (272B) lighting segments.

EXAMPLES

Lab experiments to evaluate the antimicrobial effect of antimicrobial light were performed. The irradiance at 405 nm was measured at each of 12 locations on a target surface using a Gentec Pronto-Si laser power meter. The average power across the array was 14.4±1.1 mW·cm$^{-2}$. Based on this average power the energy impinging on the sample wells over time was used to calculate antimicrobial light exposure in the sample wells.

| t/min | J·cm$^{-2}$ Gentec |
|---|---|
| 10 | 8.6 |
| 20 | 17.3 |
| 30 | 25.9 |
| 45 | 38.9 |
| 60 | 51.8 |
| 65 | 56.2 |
| 90 | 77.8 |
| 120 | 103.7 |

Results of evaluating/understanding the efficacy of antimicrobial light in liquid media using common organisms in a liquid environment (*Pseudomonas fluorescens, E. coli, Saccharomyces cerevisiae, Candida albicans*) are shown in the following tables:

| Test (antimicrobial test fixture/Liquid media) Tested Organisms | Replicate | Log (CFU) Survivors/ml | | | | | |
|---|---|---|---|---|---|---|---|
| | | After 30 m | After 1 h | After 2 h | After 4 h | After 6 h | After 24 h |
| E. coli | R1 | 4.78 | 4.63 | 3.82 | 2.95 | 2.87 | 0.00 |
| E. coli | R2 | 4.80 | 4.54 | 3.99 | 3.15 | 2.76 | 0.00 |
| P. fluorescens | R1 | 3.34 | 2.48 | 0.00 | 0.00 | 0.00 | 0.00 |
| P. fluorescens | R2 | 3.08 | 1.00 | 0.00 | 0.00 | 0.00 | 0.00 |
| C. albicans | R1 | 4.72 | 4.84 | 3.84 | 2.92 | 2.79 | 0.30 |
| C. albicans | R2 | 4.83 | 4.84 | 3.88 | 2.86 | 2.64 | 0.00 |
| S. cerevisiae | R1 | 4.51 | 4.51 | 4.05 | 3.52 | 3.40 | 0.00 |
| S. cerevisiae | R2 | 4.61 | 4.58 | 3.91 | 3.60 | 3.32 | 0.00 |

| Control (no light/Liquid media) Tested Organisms | Replicate | Log (CFU) Survivors/ml | | | | | |
|---|---|---|---|---|---|---|---|
| | | After 30 m | After 1 h | After 2 h | After 4 h | After 6 h | After 24 h |
| E. coli | R1 | 5.00 | 4.97 | 5.09 | 5.02 | 5.17 | 5.98 |
| E. coli | R2 | 5.02 | 5.06 | 4.81 | 5.11 | 5.12 | 5.94 |
| P. fluorescens | R1 | 4.85 | 4.82 | 4.92 | 5.04 | 5.11 | 5.10 |
| P. fluorescens | R2 | 4.83 | 4.83 | 4.89 | 5.14 | 5.01 | 5.28 |
| C. albicans | R1 | 4.75 | 4.61 | 4.67 | 4.95 | 4.92 | 5.84 |
| C. albicans | R2 | 4.73 | 4.82 | 4.77 | 4.94 | 4.88 | 5.85 |
| S. cerevisiae | R1 | 4.88 | 4.75 | 4.83 | 4.88 | 4.85 | 5.08 |
| S. cerevisiae | R2 | 4.90 | 4.72 | 4.81 | 4.90 | 4.91 | 4.76 |

Results of evaluating the efficacy of antimicrobial light on a dried surface (stainless steel coupon) for common organisms (*Pseudomonas fluorescens, E. coli, Candida albicans*) are shown in the following tables:

| Test (antimicrobial test fixture/Stainless steel coupon) Tested Organisms | Replicate | Log (CFU) Survivors/Carrier | | | |
|---|---|---|---|---|---|
| | | After 5.5 h | After 24 h | After 48 h | After 72 h |
| E. coli | R1 | 5.88 | 1.40 | 1.40 | 1.40 |
| E. coli | R2 | 5.60 | 1.40 | 1.40 | 1.40 |
| P. fluorescens | R1 | 4.98 | 3.92 | 1.40 | 1.40 |
| P. fluorescens | R2 | 5.48 | 1.40 | 1.40 | 1.40 |
| C. albicans | R1 | 4.74 | 2.85 | 1.40 | 1.40 |
| C. albicans | R2 | 4.17 | 3.90 | 1.40 | 1.40 |

| Control (no light/Stainless steel coupon) Tested Organisms | Replicate | Log (CFU) Survivors/Carrier | | | |
|---|---|---|---|---|---|
| | | After 5.5 h | After 24 h | After 48 h | After 72 h |
| E. coli | R1 | 7.27 | 7.28 | 6.94 | 6.43 |
| E. coli | R2 | 7.27 | 7.30 | 6.99 | 6.28 |
| P. fluorescens | R1 | 6.93 | 7.14 | 7.16 | 6.02 |
| P. fluorescens | R2 | 7.02 | 7.15 | 6.69 | 6.29 |
| C. albicans | R1 | 5.45 | 5.42 | 5.12 | 4.24 |
| C. albicans | R2 | 5.08 | 5.32 | 5.05 | 5.00 |

Result Discussion

Liquid Media Test Results showed a complete reduction of bacteria and yeast residues in liquid media (from 5 log to zero log) within 24 hours of exposure to antimicrobial light compared to the control result.

Stainless Steel Coupons Test Result showed a complete reduction of bacteria and yeast residues on hard surfaces (from 5 log to 1 log —minimum detectable limit) within 48 hours of exposure to antimicrobial light compared to the control result.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable gate arrays (FPGAs), or other equivalent integrated or discrete logic circuitry. Accordingly, the terms "processor" and "processing circuitry" as used herein may refer to any of the foregoing structures or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

Various components, modules, or units are described in this disclosure to emphasize functional aspects of devices configured to perform the disclosed techniques, but do not necessarily require realization by different hardware units. Rather, as described above, various units may be combined in a single hardware unit or provided by a collection of interoperative hardware units, including one or more processors as described above, in conjunction with suitable software and/or firmware.

ADDITIONAL EXAMPLES

Example 1

A system comprising a lighting array including one or more antimicrobial lighting segments, each antimicrobial lighting segment including one or more light source elements that emit light within one or more antimicrobial wavelength ranges; and a lighting controller comprising: one or more processors; and a data storage device comprising instructions that when executed by the one or more processors cause the one or more processors to: receive object type information associated with a common touch object; and control each antimicrobial lighting segment such that the antimicrobial light array delivers antimicrobial light sufficient to inactivate one or more microorganisms on one or more common touch surface(s) on the common touch object based on the received object type information.

Example 2

The system of Example 1 wherein object type information is input by a user.

Example 3

The system of Example 1 wherein the object type information is indicative that the common touch object is one of a restaurant menu, airline safety instructions, or instructions for use (IFUs).

Example 4

The system of Example 1 wherein the common touch object has a flat and/or folded form factor.

Example 5

The system of Example 4 wherein the one or more processors activate one or more of the antimicrobial lighting segments and deactivate one or more of the antimicrobial lighting segments based on the object type information.

Example 6

The system of Example 1 further including a housing including a cover, a base, and one or more sidewalls, the housing defining an enclosed decontamination chamber; the housing further including a slot in one of the sidewalls sized to receive a common touch object, wherein the antimicrobial light segments are arranged to direct antimicrobial light toward a decontamination area within the decontamination chamber, and wherein the common touch object is placed within the decontamination area during an antimicrobial light treatment.

Example 7

The system of Example 6 wherein the one or more antimicrobial lighting segments are disposed within the decontamination chamber to direct light at the wavelength and irradiance sufficient to inactivate one or more microorganisms on one or more common touch surfaces on the common touch object.

Example 8

The system of Example 1 wherein each antimicrobial lighting segment includes a substrate and a plurality of light-emitting diode (LED) elements.

Example 9

The system of Example 1, wherein each antimicrobial lighting segment includes a substrate and a plurality of light-emitting diode (LED) elements, and wherein each LED element emits antimicrobial light within a first wavelength range of about 380-420 nanometers and having a peak wavelength of about 405 nanometers.

Example 10

The system of Example 9, wherein the plurality of LED elements are arranged in a linear pattern on the substrate.

Example 11

The system of Example 9, wherein the plurality of LED elements are arranged in a grid pattern on the substrate.

Example 12

The system of Example 9, wherein the substrate is one of a flexible substrate or a rigid substrate.

Example 13

The system of Example 1, wherein each antimicrobial lighting segment includes a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-380 nanometers.

Example 14

The system of Example 1, wherein each antimicrobial lighting segment includes a substrate and a plurality of light-emitting diode (LED) elements, wherein one or more of the LED elements emit light within a first antimicrobial wavelength range of about 380-420 nanometers, one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

Example 15

The system of Example 1 wherein the data storage device further comprises instructions that when executed by the one or more processors cause the one or more processors to: receive dimensional information associated with the common touch object; and control each antimicrobial lighting segment such that the antimicrobial light array delivers antimicrobial light sufficient to inactivate one or more microorganisms on one or more common touch surface(s) on the common touch object based on the received dimensional information.

Example 16

The system of Example 1 wherein the common touch object includes a first common touch surface and an oppositely facing second common touch surface and wherein the system further comprises a housing forming an enclosed chamber sized to receive the common touch object; and an array of one or more antimicrobial light segments arranged within the chamber to form a first grid pattern of antimicrobial light source elements sized to irradiate the first common touch surface and arranged to form a second grid pattern of antimicrobial light source elements sized to irradiate the second common touch surface.

Example 17

The system of Example 16 wherein the antimicrobial light segments are controllable to irradiate the first and second common touch surfaces simultaneously.

Example 18

The system of Example 16 wherein the antimicrobial light segments are controllable to irradiate the first and second common touch surfaces in sequence.

Example 19

A method comprising disposing a lighting array including one or more antimicrobial lighting segments, each antimicrobial lighting segment including one or more light source elements, wherein each light source element emits antimicrobial light within one or more antimicrobial wavelength ranges; receiving object type information associated with a common touch object; and controlling each antimicrobial lighting segment such that the antimicrobial light array delivers antimicrobial light sufficient to inactivate one or more microorganisms on one or more common touch surface(s) on the common touch object based on the received object type information.

Example 20

The system of Example 19, wherein each antimicrobial lighting segment includes a substrate and a plurality of light-emitting diode (LED) elements, and wherein one or more of the LED elements emit light within a first antimicrobial wavelength range of about 380-420 nanometers and having a peak wavelength of about 405 nanometers.

Example 21

The system of Example 20, wherein one or more of the LED elements emit light within a second antimicrobial wavelength range of about 200-280 nanometers.

Various examples have been described. These and other examples are within the scope of the following claims.

The invention claimed is:

1. A system comprising:
   a lighting array including a plurality of antimicrobial lighting segments, each of the antimicrobial lighting segments including one or more light source elements configured to emit antimicrobial light within one or more antimicrobial wavelength ranges; and
   a lighting controller comprising one or more processors configured to:
   receive object type information associated with a touch object, wherein the object type information specifies at least one of a type of the touch object or a material of the touch object;
   determine, based on the object type information, a dosage to be applied by the lighting array to inactivate one or more microorganisms on one or more touch surfaces on the touch object, wherein the one or more processors are configured to, as part of determining the dosage, determine antimicrobial wavelengths for an antimicrobial light treatment, the determined antimicrobial wavelengths being within the one or more antimicrobial wavelength ranges; and
   activate selected antimicrobial lighting segments of the plurality of antimicrobial lighting segments such that the lighting array applies the determined dosage to the touch surfaces on the touch object.

2. The system of claim 1, wherein the one or more processors are configured to receive the object type information as input from a user.

3. The system of claim 1, wherein the object type information is indicative that the touch object is one of a restaurant menu, airline safety instructions, or instructions for use (IFUs).

4. The system of claim 1, wherein the touch object has a folded form factor.

5. The system of claim 4, wherein the one or more processors are configured to activate one or more of the antimicrobial lighting segments and deactivate one or more of the antimicrobial lighting segments based on the object type information.

6. The system of claim 1, further including a housing including a cover, a base, and one or more sidewalls, wherein:
the housing defines an enclosed decontamination chamber,
the housing further defines a slot in one of the sidewalls sized to receive the touch object, and
the antimicrobial lighting segments are arranged to direct antimicrobial light toward a decontamination area within the decontamination chamber, and wherein the touch object is placed within the decontamination chamber during the antimicrobial light treatment.

7. The system of claim 6, wherein the antimicrobial lighting segments are disposed within the decontamination chamber to direct the antimicrobial light at the determined antimicrobial wavelengths and irradiance sufficient to inactivate the one or more microorganisms on the one or more touch surfaces on the touch object.

8. The system of claim 1, wherein at least one antimicrobial lighting segment of the plurality of antimicrobial lighting segments includes a substrate and the one or more light source elements of the antimicrobial lighting segment include a plurality of light-emitting diode (LED) elements on the substrate.

9. The system of claim 1, wherein:
the one or more antimicrobial wavelength ranges includes a first antimicrobial wavelength range of about 380-420 nanometers and has a peak wavelength of about 405 nanometers, and
at least one antimicrobial lighting segment of the plurality of antimicrobial lighting segments includes a substrate and the one or more light source elements of the antimicrobial lighting segment include a plurality of light-emitting diode (LED) elements, and each LED element of the plurality of LED elements is configured to emit the antimicrobial light within the first antimicrobial wavelength range.

10. The system of claim 9, wherein the plurality of LED elements of the antimicrobial lighting segment are arranged in a linear pattern on the substrate of the antimicrobial lighting segment.

11. The system of claim 9, wherein the plurality of LED elements of the antimicrobial lighting segment are arranged in a grid pattern on the substrate of the antimicrobial lighting segment.

12. The system of claim 9, wherein the substrate is one of a flexible substrate or a rigid substrate.

13. The system of claim 1, wherein:
the one or more antimicrobial wavelength ranges includes a first antimicrobial wavelength range of about 380-420 nanometers,
the one or more antimicrobial wavelength ranges includes a second antimicrobial wavelength range of about 200-280 nanometers,
at least one antimicrobial lighting segment of the plurality of antimicrobial lighting segments includes a substrate and the one or more light source elements of the antimicrobial lighting segment include a plurality of light-emitting diode (LED) elements on the substrate,
one or more of the LED elements are configured to emit a first component of the antimicrobial light within the first antimicrobial wavelength range, and
one or more of the LED elements are configured to emit a second component of the antimicrobial light within the second antimicrobial wavelength range.

14. The system of claim 1, wherein:
the one or more antimicrobial wavelength ranges includes a first antimicrobial wavelength range of about 380-420 nanometers,
the one or more antimicrobial wavelength ranges includes a second antimicrobial wavelength range including at least one of ultraviolet A (UVA) light within a wavelength range of 315-400 nm, ultraviolet B (UVB) light within a wavelength range of 280-315 nm, or ultraviolet C (UVC) light within a wavelength range of 200-280 nm,
at least one antimicrobial lighting segment of the plurality of antimicrobial lighting segments includes a substrate and the one or more light source elements of the antimicrobial lighting segment includes a plurality of light-emitting diode (LED) elements on the substrate,
one or more of the LED elements are configured to emit light within the first antimicrobial wavelength range, and
one or more of the LED elements are configured to emit the antimicrobial light within the second antimicrobial wavelength range.

15. The system of claim 1, wherein the touch object is a first touch object and the one or more processors are configured to:
receive dimensional information associated with a second touch object; and
control each of the antimicrobial lighting segments such that the lighting array delivers an amount of the antimicrobial light sufficient to inactivate one or more microorganisms on one or more touch surfaces on the second touch object based on the received dimensional information.

16. The system of claim 1, wherein the touch object includes a first touch surface and an oppositely facing second touch surface and wherein the system further comprises:
a housing forming an enclosed chamber sized to receive the touch object; and
the antimicrobial lighting segments are arranged within the chamber to form a first grid pattern of the light source elements sized to irradiate the first touch surface and are arranged to form a second grid pattern of the light source elements sized to irradiate the second touch surface.

17. The system of claim 16, wherein the antimicrobial lighting segments are controllable to irradiate the first and second touch surfaces simultaneously.

18. The system of claim 16, wherein the antimicrobial lighting segments are controllable to irradiate the first and second touch surfaces in sequence.

19. A method comprising:
disposing a lighting array including a plurality of antimicrobial lighting segments, each of the antimicrobial lighting segments including one or more light source elements, wherein each of the light source elements is configured to emit antimicrobial light within one or more antimicrobial wavelength ranges;

receiving object type information associated with a touch object, wherein the object type information specifies at least one of a type of the touch object or a material of the touch object;

determining, based on the object type information, a dosage to be applied by the lighting array to inactivate one or more microorganisms on one or more touch surfaces on the touch object, wherein determining the dosage comprises determining antimicrobial wavelengths for an antimicrobial light treatment, the determined antimicrobial wavelengths being within the one or more antimicrobial wavelength ranges; and activating selected antimicrobial lighting segments of the plurality of antimicrobial lighting segments such that the lighting array applies the determined dosage to the touch surfaces on the touch object.

20. The method of claim 19, wherein:

the one or more antimicrobial wavelength ranges include a first antimicrobial wavelength range of about 380-420 nanometers and has a peak wavelength of about 405 nanometers, at least one antimicrobial lighting segment of the antimicrobial lighting segments includes a substrate and the light source elements of the antimicrobial lighting segment include a plurality of light-emitting diode (LED) elements on the substrate, and one or more of the LED elements are configured to emit at least a component of the antimicrobial light within the first antimicrobial wavelength range.

21. The method of claim 20, wherein:

the one or more antimicrobial wavelength ranges include a second antimicrobial wavelength range of about 200-280 nanometers, the component of the antimicrobial light is a first component of the antimicrobial light, and one or more of the LED elements are configured to emit a second component of the antimicrobial light within the second antimicrobial wavelength range.

* * * * *